US00RE47000E

(19) United States
(12) Reissued Patent
Saitoh

(10) Patent Number: US RE47,000 E
(45) Date of Reissued Patent: Aug. 21, 2018

(54) OPTICAL ELEMENT COMPOUND, OPTICAL MATERIAL, AND OPTICAL ELEMENT

(71) Applicant: CANON KABUSHIKI KAISHA, Tokyo (JP)

(72) Inventor: Terunobu Saitoh, Kawasaki (JP)

(73) Assignee: Canon Kabushiki Kaisha, Tokyo (JP)

(21) Appl. No.: 14/927,209

(22) Filed: Oct. 29, 2015

Related U.S. Patent Documents

Reissue of:
(64) Patent No.: 8,569,541
Issued: Oct. 29, 2013
Appl. No.: 13/112,474
Filed: May 20, 2011

(30) Foreign Application Priority Data

May 24, 2010 (JP) ..... 2010-118823
Feb. 9, 2011 (JP) ..... 2011-026381

(51) Int. Cl.
*C07C 69/73* (2006.01)
*G02B 1/04* (2006.01)
*C07C 69/602* (2006.01)

(52) U.S. Cl.
CPC ..... *G02B 1/04* (2013.01); *G02B 1/041* (2013.01); *C07C 69/602* (2013.01); *C07C 69/73* (2013.01)

(58) Field of Classification Search
CPC ..... G02B 1/04; G02B 1/041; C08L 81/00; C08L 33/10; C07C 69/73; C07C 69/602
See application file for complete search history.

(56) References Cited

U.S. PATENT DOCUMENTS

| | | | | |
|---|---|---|---|---|
| 8,829,230 | B2 * | 9/2014 | Saitoh | G02B 1/04 560/221 |
| 2007/0078198 | A1 | 4/2007 | Otsuji | |
| 2008/0200582 | A1 * | 8/2008 | Craciun et al. | 522/166 |
| 2010/0076106 | A1 | 3/2010 | Iwasa | |

FOREIGN PATENT DOCUMENTS

| | | | |
|---|---|---|---|
| CN | 1775779 | A | 5/2006 |
| CN | 101685166 | A | 3/2010 |
| JP | H01-167315 | A | 7/1989 |
| JP | H02-133415 | A | 5/1990 |
| JP | 2008-158361 | A | 7/2008 |
| WO | 2010/018858 | A1 | 2/2010 |

OTHER PUBLICATIONS

Machine translation of JP 01-167315 A.*
170275-06-6_CAS Registry[online]_STN International_p. 1.
CAS Registry [online] 124950-02-3, Entered Jan. 26, 1990.

* cited by examiner

*Primary Examiner* — Jerry D Johnson
(74) *Attorney, Agent, or Firm* — Canon U.S.A. Inc., IP Division

(57) ABSTRACT

An optical material organic compound having characteristics that the dispersion characteristic (Abbe number ($\nu_d$)) and the secondary dispersion characteristic (θg,F) of the refractive index are high, the transmittance in the visible light region is high, and the chromatic aberration correction function delivers high performance, which represented by the general formula (1) or (2) is provided.

20 Claims, 2 Drawing Sheets

OPTICAL ELEMENT COMPOUND, OPTICAL MATERIAL, AND OPTICAL ELEMENT

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS REFERENCE*

*This is an application for reissue of U.S. Pat. No. 8,569,541. Notice: More than one reissue application has been filed for the reissue of U.S. Pat. No. 8,569,541. The reissue applications are U.S. patent application Ser. No. 14/927,209 (the present application) and U.S. patent application Ser. No. 15/681,241, where U.S. patent application Ser. No. 15/681,241 is a divisional reissue of U.S. patent application Ser. No. 14/927,209.*

BACKGROUND OF THE INVENTION

1. Field of the Invention

The present invention relates to an optical material organic compound as well as an optical material and an optical element by using the optical element compound. In particular, the present invention relates to a (meth)acrylate compound having peculiar optical characteristics as well as an optical material and an optical element by using the (meth)acrylate compound.

2. Description of the Related Art

In general, the refractive indices of optical materials composed of glass materials, organic resins, or the like increase gradually with decreasing wavelengths. Examples of indicators representing the chromatic dispersion property of the refractive index include an Abbe number ($\nu_d$) and a secondary dispersion characteristic (θg,F). The Abbe number and the value of θg,F are values peculiar to individual optical materials and fall within certain ranges in many cases. FIG. 1 is a diagram showing the relationship between the secondary dispersion characteristic (θg,F) and the Abbe number of organic materials (glass materials and organic resins) in the related art.

In this regard, the Abbe number ($\nu_d$) and the secondary dispersion characteristic (θg,F) are represented by the following formulae.

$$\text{Abbe number } (\nu_d)=(n_d-1)/(n_F-n_c)$$

$$\text{secondary dispersion characteristic } (\theta g,F)=(n_g-n_F)/(n_F-n_c)$$

($n_d$ represents a refractive index at a wavelength of 587.6 nm, $n_F$ represents a refractive index at a wavelength of 486.1 nm, $n_c$ represents a refractive index at a wavelength of 656.3 nm, and $n_g$ represents a refractive index at a wavelength of 435.8 nm)

Meanwhile, optical materials (glass materials, organic resins, and the like) having excellent optical characteristics (high θg,F characteristic) out of the above-described certain range have also been proposed on the basis of detailed by design of the configuration (material species and molecular structure) of the optical materials. For example, polyvinyl carbazole, which is shown by A in FIG. 1 and which is an organic resin, has a secondary dispersion characteristic (high θg,F characteristic) higher than that of common organic resin materials.

In general, in a dioptric system, it is possible to reduce chromatic aberration by combining glass materials having different dispersion characteristics appropriately. For example, regarding an objective lens of a telescope or the like, chromatic aberration, which appears on an axis, is corrected by using a glass material having small dispersion and serving as a positive lens element and a glass material having large dispersion and serving as a negative lens element in combination. However, for example, in the case where the configuration and the number of lenses are limited and in the case where glass material used are limited, it may become very difficult to correct the chromatic aberration sufficiently. As for one method to solve such a problem, there is a method by making full use of a glass material having an anomalous dispersion characteristic. Optical elements have been designed by using this method.

In the case where an optical element having an excellent chromatic aberration correction function and having the shape of an aspherical surface or the like is produced, for example, molding of an organic resin on spherical glass or the like has an advantage that the mass-productivity, the moldability, the flexibility in shape, and the light-weight property are excellent as compared with use of the glass material as the material. However, the optical characteristics of the organic resin in the related art fall within a certain limited range (the secondary dispersion characteristic (θg,F) is 0.700 or less) as shown in FIG. 1, and organic resins exhibiting peculiar dispersion characteristics are very few.

Against the above-described background, in Japanese Patent Laid-Open No. 2008-158361, an optical resin composition produced by mixing N-acryloylcarbazole, a polyfunctional polyester acrylate, dimethylol tricyclodecane diacrylate, and a polymerization initiator at a predetermined ratio has been proposed. Furthermore, Japanese Patent Laid-Open No. 2008-158361 has reported that the above-described optical resin composition is worked easily and a cured product serves as a material having sufficient anomalous dispersion and durability.

However, a material having characteristics (high θg,F characteristic) within the area indicated by B in FIG. 1 and practicality (low colorability, high transparency) is not present now. Moreover, every material proposed in Japanese Patent Laid-Open No. 2008-158361 has a θg,F value of 0.70 or less.

SUMMARY OF THE INVENTION

The present invention has been made in consideration of the above-described background art. The present invention provides an optical organic material compound having characteristics that the dispersion characteristic (Abbe number ($\nu_d$)) and the secondary dispersion characteristic (θg,F) of the refractive index are high, the transmittance in the visible light region is high, and the chromatic aberration correction function delivers high performance.

An optical material organic compound according to the present invention is a compound represented by the following general formula (1) or (2):

(1)

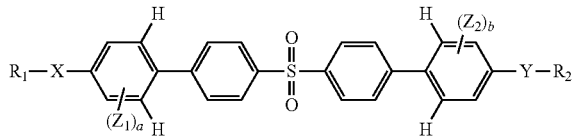

-continued (2)

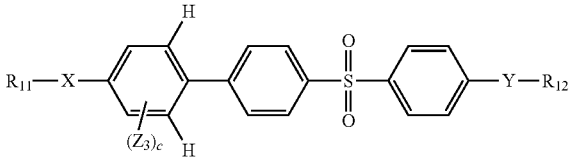

in the formula (1), X and Y represent individually a substituent selected from the following substituents,

| | |
|---|---|
| *—S— | *—O— |
| *—O—$CH_2CH_2$—O— | *—O—$CH_2CH_2$—S— |
| *—S—$CH_2CH_2$—O— | *—S—$CH_2CH_2$—S— |
| *—O—$CH_2CH_2CH_2$—O— | *—O—$CH_2CH_2CH_2$—S— |
| *—S—$CH_2CH_2CH_2$—O— | *—S—$CH_2CH_2CH_2$—S— |
| *—S—$CH_2CH_2CH_2CH_2$—S— | *—O—$CH_2CH_2CH_2CH_2$—O— |
| *—O—$CH_2CH_2CH_2CH_2$—S— | *—S—$CH_2CH_2CH_2CH_2$—O— |

where a symbol * represents an end bonded to $R_1$ or $R_2$, $R_1$ and $R_2$ represent individually a substituent selected from the group consisting of a hydrogen atom, an alkyl group having the carbon number of 1 or 2, and a (meth)acryloyl group, $Z_1$ and $Z_2$ represent individually a substituent selected from the group consisting of a hydrogen atom, a halogen atom, an alkoxy group having the carbon number of 1 or 2, an alkylthio group having the carbon number of 1 or 2, and a substituted or unsubstituted alkyl group having the carbon number of 1 or 2, a and b represent individually an integer of 0 to 2, two $Z_1$s may be the same or different when a is 2, and two $Z_2$s may be the same or different when b is 2.

In the general formula (2), X represents a substituent selected from the following substituents,

| | |
|---|---|
| *—S— | |
| *—S—$CH_2CH_2$—S— | *—O—$CH_2CH_2$—S— |
| *—S—$CH_2CH_2CH_2$—O— | *—O—$CH_2CH_2CH_2$—S— |
| *—S—$CH_2CH_2CH_2CH_2$—S— | *—O—$CH_2CH_2CH_2CH_2$—S— |

where a symbol * represents an end bonded to $R_{11}$, Y represents a substituent selected from the following substituents,

| | |
|---|---|
| *—S— | *—O— |
| *—O—$CH_2CH_2$—O— | *—O—$CH_2CH_2$—S— |
| *—S—$CH_2CH_2$—O— | *—S—$CH_2CH_2$—S— |
| *—O—$CH_2CH_2CH_2$—O— | *—O—$CH_2CH_2CH_2$—S— |
| *—S—$CH_2CH_2CH_2$—O— | *—S—$CH_2CH_2CH_2$—S— |
| *—O—$CH_2CH_2CH_2CH_2$—S— | *—O—$CH_2CH_2CH_2CH_2$—O— |
| *—S—$CH_2CH_2CH_2CH_2$—S— | *—S—$CH_2CH_2CH_2CH_2$—O— |

where a symbol * represents an end bonded to $R_{12}$, $R_{11}$ and $R_{12}$ represent individually a substituent selected from the group consisting of a hydrogen atom, an alkyl group having the carbon number of 1 or 2, and a (meth)acryloyl group, $Z_3$ represents a substituent selected from the group consisting of a hydrogen atom, a halogen atom, an alkoxy group having the carbon number of 1 or 2, an alkylthio group having the carbon number of 1 or 2, and a substituted or unsubstituted alkyl group having the carbon number of 1 or 2, c represents an integer of 0 to 2, and two $Z_3$s may be the same or different when c is 2.

According to the present invention, an optical material organic compound having characteristics that the dispersion characteristic (Abbe number ($\nu_d$)) and the secondary dispersion characteristic (θg,F) of the refractive index are high and the chromatic aberration correction function delivers high performance can be provided.

Consequently, an optical element produced by molding the optical material including the optical material organic compound according to the present invention can eliminate chromatic aberration efficiently. Therefore, according to the present invention, an optical system can be made more lightweight and compact.

Further features of the present invention will become apparent from the following description of exemplary embodiments with reference to the attached drawings.

DESCRIPTION OF THE EMBODIMENTS

Figure 1:
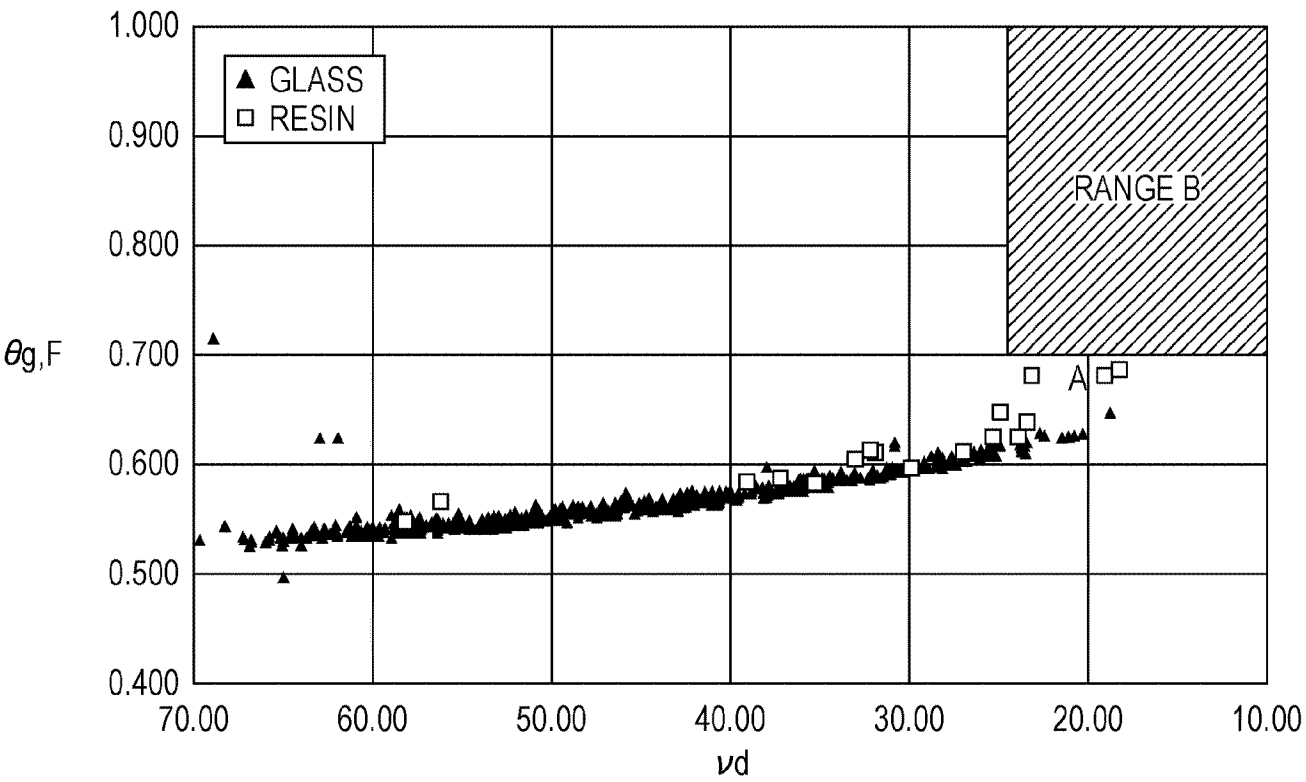
FIG. 1 is a graph showing the relationship between the secondary dispersion characteristics and the Abbe numbers of commercially available optical materials.

The present invention will be described below in detail. An optical material organic compound according to the present invention is a compound represented by the following general formula (1) or general formula (2).

(1)

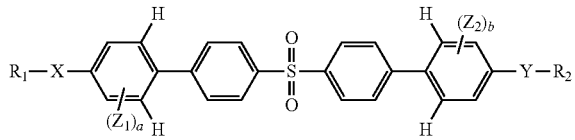

(2)

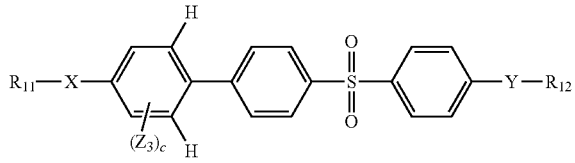

The optical material organic compound according to the present invention is a compound having a partial structure represented by the following (1A) or (2A) as a basic skeleton and can be a (meth)acrylate compound having the partial structure represented by the following (1A) or (2A) and a (meth)acryloyl group, (1A)

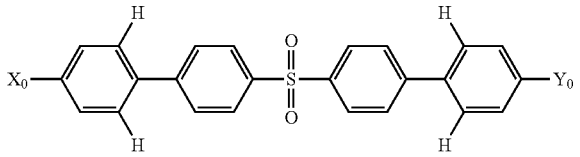

(2A)

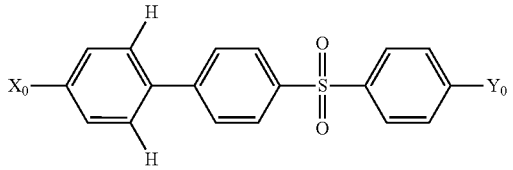

in the general formula (2A) and the general formula (3A), $X_0$ and $Y_0$ represent individually an oxygen atom or a sulfur atom.

In this regard, embodiments of the optical material organic compound according to the present invention will be described later.

Initially, a compound represented by the general formula (1) will be described. In the general formula (1), X and Y represent individually a substituent selected from the following substituents.

| | |
|---|---|
| *—S— | *—O— |
| *—O—$CH_2CH_2$—O— | *—O—$CH_2CH_2$—S— |
| *—S—$CH_2CH_2$—O— | *—S—$CH_2CH_2$—S— |
| *—O—$CH_2CH_2CH_2$—O— | *—O—$CH_2CH_2CH_2$—S— |
| *—S—$CH_2CH_2CH_2$—O— | *—S—$CH_2CH_2CH_2$—S— |
| *—S—$CH_2CH_2CH_2CH_2$—S— | *—O—$CH_2CH_2CH_2CH_2$—O— |
| *—O—$CH_2CH_2CH_2CH_2$—S— | *—S—$CH_2CH_2CH_2CH_2$—O— |

Regarding the substituent represented by X and Y in the general formula (1), a symbol * represents a hand (an end) bonded to $R_1$ or $R_2$.

In the general formula (1), $R_1$ and $R_2$ represent individually a substituent selected from the group consisting of a hydrogen atom, an alkyl group having the carbon number of 1 or 2, and a (meth)acryloyl group.

As for alkyl groups represented by $R_1$ and $R_2$, a methyl group and an ethyl group are mentioned.

In the general formula (1), $Z_1$ and $Z_2$ represent individually a substituent selected from the group consisting of a hydrogen atom, a halogen atom, an alkoxy group having the carbon number of 1 or 2, an alkylthio group having the carbon number of 1 or 2, and a substituted or unsubstituted alkyl group having the carbon number of 1 or 2.

As for the halogen atoms represented by $Z_1$ and $Z_2$, fluorine, chlorine, bromine, and iodine are mentioned.

As for the alkoxy groups represented by $Z_1$ and $Z_2$, a methoxy group and an ethoxy group are mentioned.

As for alkylthio groups represented by $Z_1$ and $Z_2$, a methylthio group and an ethylthio group are mentioned.

As for the alkyl groups represented by $Z_1$ and $Z_2$, a methyl group and an ethyl group are mentioned. Furthermore, this alkyl group may have a substituent selected from the group consisting of a (meth)acryloyloxy group, a (meth)acryloyloxyethoxy group, a 2-hydroxyethoxy group, a 2-mercaptoethoxy group, a 2-mercaptoethylthio group, a (meth)acryloyloxypropoxy group, a 3-hydroxypropoxy group, a 3-mercaptopropoxy group, a 3-mercaptopropylthio group, a (meth)acryloyloxybutoxy group, a 4-hydroxybutoxy group, a 4-mercaptobutoxy group, a 4-mercaptobutylthio group, an allyloxy group, an allylthio group, a 4-vinylbenzyloxy group, an oxiranyl methoxy group, an oxiranyl ethoxy group, a thiiranyl methoxy group, a thiiranyl ethoxy group, a methylthio group, an ethylthio group, a methoxy group, and an ethoxy group.

In the general formula (1), a and b represent individually an integer of 0 to 2. Here, two $Z_1$s may be the same or different when a is 2, and two $Z_2$s may be the same or different when b is 2. In consideration of ease of synthesis, a and b can be individually 0 or 1.

Next, embodiments of the compound represented by the general formula (1) will be described. The embodiments of the compound represented by the general formula (1) can be roughly divided into items (1-1) and (1-2) described below.

(1-1) Case where X and Y represent individually a substituent selected from the following substituents

| | |
|---|---|
| *—O—$CH_2CH_2$—O— | *—O—$CH_2CH_2$—S— |
| *—S—$CH_2CH_2$—O— | *—S—$CH_2CH_2$—S— |
| *—O—$CH_2CH_2CH_2$—O— | *—O—$CH_2CH_2CH_2$—S— |
| *—S—$CH_2CH_2CH_2$—O— | *—S—$CH_2CH_2CH_2$—S— |
| *—S—$CH_2CH_2CH_2CH_2$—S— | *—O—$CH_2CH_2CH_2CH_2$—O— |
| *—O—$CH_2CH_2CH_2CH_2$—S— | *—S—$CH_2CH_2CH_2CH_2$—O— |

(1-2) Case where X and Y represent individually a sulfur atom (—S—) or an oxygen atom (—O—)

An embodiment according to the item (1-1) can satisfy the following items (1-1-1) to (1-1-3).

(1-1-1) X and Y represent individually a substituent selected from the following substituents

| | |
|---|---|
| *—O—$CH_2CH_2$—O— | *—O—$CH_2CH_2$—S— |
| *—O—$CH_2CH_2CH_2$—O— | *—O—$CH_2CH_2CH_2$—S— |
| *—O—$CH_2CH_2CH_2CH_2$—S— | *—O—$CH_2CH_2CH_2CH_2$—O— |

(1-1-2) $R_1$ and $R_2$ represent individually a substituent selected from the group consisting of a hydrogen atom, an alkyl group having the carbon number of 1 or 2, and a (meth)acryloyl group (1-1-3) $Z_1$ and $Z_2$ represent individually a substituent selected from the group consisting of a hydrogen atom, a halogen atom, an alkoxy group having the carbon number of 1 or 2, an alkylthio group having the carbon number of 1 or 2, and a substituted or unsubstituted alkyl group having the carbon number of 1 or 2

In particular, an embodiment according to the item (1-1) can satisfy the above-described item (1-1-1) and the following items (1-1-4) and (1-1-5).

(1-1-4) $R_1$ and $R_2$ represent individually hydrogen or a (meth)acryloyl group (1-1-5) $Z_1$ and $Z_2$ represent individually a substituent selected from the group consisting of a hydrogen atom, a halogen atom, an alkoxy group having the carbon number of 1 or 2, an alkylthio group having the carbon number of 1 or 2, and an alkyl group having the carbon number of 1 or 2

In the case of the item (1-2), the following items (1-2-1) to (1-2-3) can be satisfied.

(1-2-1) X and Y represent individually —S— or —O—

(1-2-2) $R_1$ and $R_2$ represent individually hydrogen or an alkyl group having the carbon number of 1 or 2

(1-2-3) $Z_1$ and $Z_2$ represent individually a substituent selected from the group consisting of a hydrogen atom, a halogen atom, an alkoxy group having the carbon number of 1 or 2, an alkylthio group having the carbon number of 1 or 2, and a substituted or unsubstituted alkyl group having the carbon number of 1 or 2

Furthermore, an embodiment according to the item (1-2) can satisfy the above-described items (1-2-1) and (1-2-2) and the following item (1-2-4).

(1-2-4) $Z_1$ and $Z_2$ represent individually a hydrogen atom or a substituted or unsubstituted alkyl group having the carbon number of 1 or 2

In particular, an embodiment according to the item (1-2) can satisfy the above-described items (1-2-1) and (1-2-4) and the following item (1-2-5).

(1-2-5) $R_1$ and $R_2$ represent individually an alkyl group having the carbon number of 1 or 2

Meanwhile, in the case where $Z_1$ and $Z_2$ represent individually an alkyl group which has a substituent and which has the carbon number of 1 or 2, the specific structure of the alkyl group can be the structure represented by the following general formula (3).

(3)

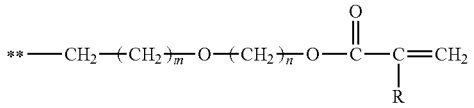

In the general formula (3), a symbol ** represents a bond, m represents 0 or 1, and n represents an integer of 2 to 4. In consideration of ease of synthesis, m can be 0. In the case where the structure of any one of $Z_1$ and $Z_2$ is the structure represented by the general formula (3), the compound in itself has a more flexible structure and, thereby, the melting point of the compound in itself can be lowered. It can be said that lowering of the melting point of the compound in itself is advantageous from the viewpoint of ease of molding.

Next, a compound represented by the general formula (2) will be described.

(2)

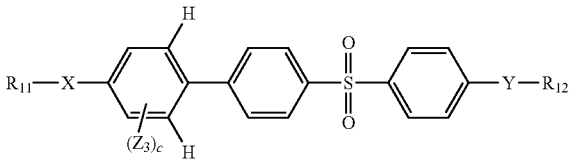

In the general formula (2), X represents a substituent selected from the following substituents.

*—S—　　*—O—$CH_2CH_2$—S—

*—S—$CH_2CH_2$—S—　　*—O—$CH_2CH_2CH_2$—S—

-continued

*—S—$CH_2CH_2CH_2$—S—　　*—O—$CH_2CH_2CH_2CH_2$—S—

*—S—$CH_2CH_2CH_2CH_2$—S—

Regarding the substituent represented by X in the general formula (2), a symbol * represents a hand (an end) bonded to $R_{11}$.

In the general formula (2), Y represents a substituent selected from the following substituents.

*—S—　　*—O—

*—O—$CH_2CH_2$—O—　　*—O—$CH_2CH_2$—S—

*—S—$CH_2CH_2$—O—　　*—S—$CH_2CH_2$—S—

*—O—$CH_2CH_2CH_2$—O—　　*—O—$CH_2CH_2CH_2$—S—

*—S—$CH_2CH_2CH_2$—O—　　*—S—$CH_2CH_2CH_2$—S—

*—O—$CH_2CH_2CH_2CH_2$—O—　　*—O—$CH_2CH_2CH_2CH_2$—S—

*—S—$CH_2CH_2CH_2CH_2$—O—　　*—S—$CH_2CH_2CH_2CH_2$—S—

Regarding the substituent represented by Y in the general formula (2), a symbol * represents a hand (an end) bonded to $R_{12}$.

In the general formula (2), $R_{11}$ and $R_{12}$ represent individually a substituent selected from the group consisting of a hydrogen atom, an alkyl group having the carbon number of 1 or 2, and a (meth)acryloyl group.

As for the alkyl groups represented by $R_{11}$ and $R_{12}$, a methyl group and an ethyl group are mentioned.

In the general formula (2), $Z_3$ represents a substituent selected from the group consisting of a hydrogen atom, a halogen atom, an alkoxy group having the carbon number of 1 or 2, an alkylthio group having the carbon number of 1 or 2, and a substituted or unsubstituted alkyl group having the carbon number of 1 or 2.

As for the alkoxy groups represented by $Z_3$, a methoxy group and an ethoxy group are mentioned.

As for alkylthio groups represented by $Z_3$, a methylthio group and an ethylthio group are mentioned.

As for the alkyl groups represented by $Z_3$, a methyl group and an ethyl group are mentioned. Furthermore, this alkyl group may have a substituent selected from the group consisting of a (meth)acryloyloxy group, a (meth)acryloyloxyethoxy group, a 2-hydroxyethoxy group, a 2-mercaptoethoxy group, a 2-mercaptoethylthio group, a (meth)acryloyloxypropoxy group, a 3-hydroxypropoxy group, a 3-mercaptopropoxy group, a 3-mercaptopropylthio group, a (meth)acryloyloxybutoxy group, a 4-hydroxybutoxy group, a 4-mercaptobutoxy group, a 4-mercaptobutylthio group, an allyloxy group, an allylthio group, a 4-vinylbenzyloxy group, an oxiranyl methoxy group, an oxiranyl ethoxy group, a thiiranyl methoxy group, a thiiranyl ethoxy group, a methylthio group, an ethylthio group, a methoxy group, and an ethoxy group.

In the general formula (2), c represents an integer of 0 to 2. Two $Z_3$s may be the same or different when c is 2. In consideration of ease of synthesis, c can be 0 or 1.

Next, embodiments of the compound represented by the general formula (2) will be described. The embodiments of the compound represented by the general formula (2) can satisfy the items (2-1) to (2-4) described below.

(2-1) X represents a substituent selected from the following substituents, $*—O—CH_2CH_2—S—$ $*—S—CH_2CH_2—S—$ $*—O—CH_2CH_2CH_2—S—$ $*—S—CH_2CH_2CH_2—S—$ $*—O—CH_2CH_2CH_2CH_2—S—$ $*—S—CH_2CH_2CH_2CH_2—S—$ (2-2) Y represents a substituent selected from the following substituents, $*—O—CH_2CH_2—O—$ $*—O—CH_2CH_2—S—$ $*—S—CH_2CH_2—O—$ $*—S—CH_2CH_2—S—$ $*—O—CH_2CH_2CH_2—O—$ $*—O—CH_2CH_2CH_2—S—$ $*—S—CH_2CH_2CH_2—O—$ $*—S—CH_2CH_2CH_2—S—$ $*—O—CH_2CH_2CH_2CH_2—O—$ $*—O—CH_2CH_2CH_2CH_2—S—$ $*—S—CH_2CH_2CH_2CH_2—O—$ $*—S—CH_2CH_2CH_2CH_2—S—$ (2-3) $R_{11}$ and $R_{12}$ represent individually a substituent selected from the group consisting of a hydrogen atom, an alkyl group having the carbon number of 1 or 2, and a (meth)acryloyl group (2-4) $Z_3$ represents a substituent selected from the group consisting of a hydrogen atom, a halogen atom, an alkoxy group having the carbon number of 1 or 2, an alkylthio group having the carbon number of 1 or 2, and a substituted or unsubstituted alkyl group having the carbon number of 1 or 2

Regarding the compounds represented by the general formula (2), furthermore, an embodiment can satisfy the above-described items (2-3) and (2-4) and the following items (2-5) and (2-6).

(2-5) X represents a substituent selected from the following substituents, $*—O—CH_2CH_2—S—$ $*—O—CH_2CH_2CH_2—S—$ $*—O—CH_2CH_2CH_2CH_2—S—$ (2-6) Y represents a substituent selected from the following substituents, $*—O—CH_2CH_2—O—$ $*—O—CH_2CH_2CH_2—O—$ $*—O—CH_2CH_2CH_2CH_2—O—$ Regarding the compounds represented by the general formula (2), in particular, an embodiment can satisfy the above-described items (2-5) and (2-6) and the following items (2-7) and (2-8).

(2-7) $R_{11}$ and $R_{12}$ represent individually a substituent selected from the group consisting of a hydrogen atom and a (meth)acryloyl group (2-8) $Z_3$ represents a substituent selected from the group consisting of a hydrogen atom, a halogen atom, an alkoxy group having the carbon number of 1 or 2, an alkylthio group having the carbon number of 1 or 2, and an alkyl group having the carbon number of 1 or 2

Meanwhile, in the case where $Z_3$ represents an alkyl group which has a substituent and which has the carbon number of 1 or 2, the specific structure of the alkyl group can be the structure represented by the following general formula (3).

$$**—CH_2—(CH_2)_m—O—(CH_2)_n—O—\overset{\overset{O}{\|}}{C}—\underset{\underset{R}{|}}{C}=CH_2 \quad (3)$$

In the general formula (3), a symbol ** represents a bond, m represents 0 or 1, and n represents an integer of 2 to 4. In consideration of ease of synthesis, m can be 0. In the case where the structure of $Z_3$ is the structure represented by the general formula (3), the compound in itself has a more flexible structure and, thereby, the melting point of the compound in itself can be lowered. It can be said that lowering of the melting point of the compound in itself is advantageous from the viewpoint of ease of molding.

Next, a method for manufacturing the optical material organic compound according to the present invention will be described with reference to an example. A production route of the optical material organic compound according to the present invention is not specifically limited, and any manufacturing method can be adopted. However, at least the following synthesis steps described in items (a) and (b) are included. Furthermore, a synthesis step described in an item (c) is included depending on a compound.

(a) Formation of bond between aromatic rings (benzene rings)

(b) Etherification (thioetherification) reaction (c) (Meth)acrylation reaction

In consideration of ease of synthesis, the above-described synthesis steps are performed in the order of (a), (b), and (c).

Regarding the synthesis step (a), modifications can be made depending on the circumstances based on the type of a functional group included in the aromatic compound. For example, a coupling reaction with a transition metal catalyst, an oxidative coupling reaction between halides, a substitution reaction on an aromatic ring, and the like are mentioned. In consideration of the reaction yield, the coupling reaction with a transition metal catalyst is desirable.

The coupling reaction with a transition metal catalyst can be selected optionally. As for typical methods, Suzuki coupling by using boric acid, Stille coupling by using organic tin, Negishi coupling by using organic zinc, and the like are used favorably.

Regarding the synthesis step (b), as for typical methods of etherification reaction, for example, a Williamson ether synthesis method, in which a hydroxyl group is converted to a salt with sodium hydroxide, potassium hydroxide, or the like and, thereafter, a corresponding halide is added, is mentioned.

Meanwhile, a thioetherification reaction is effected by a thiol group generation reaction and a reaction between a thiol group and a halide. Here, the thiol group generation reaction is achieved by, for example, converting a hydroxyl group to a substituent (TsO—, Cl—, $CF_3S(=O)_2—O—$ or the like) active with respect to a nucleophilic substitution reaction and, thereafter, effecting the nucleophilic substitution reaction by using a sulfide ion ($S^{2-}$). Furthermore, regarding the reaction between a thiol group and a halide, the above-described Williamson ether synthesis method or the like can be applied.

Regarding the synthesis step (c), as for typical methods, a method in which an hydroxyl group is esterified by using a (meth)acrylic halide or a (meth)acrylic acid anhydride, a transesterification reaction by using an ester of a lower alcohol of (meth)acrylic acid, a direct esterification reaction in which (meth)acrylic acid and a diol are dehydrated and condensed by using a condensation agent, e.g., N,N'-dicyclohexylcarbodiimide, a method in which (meth)acrylic acid and a diol concerned are heated in the presence of a dehydrating agent, e.g., sulfuric acid, and the like are used favorably.

In the case where the optical material organic compound according to the present invention is a (meth)acrylate compound, a polymerization inhibitor may be used as necessary in order that polymerization does not proceed during reaction and during preservation. Examples of polymerization inhibitors can include hydroquinones, e.g., p-benzoquinone, hydroquinone, hydroquinone monomethyl ether, and 2,5-diphenyl-p-benzoquinone, N-oxyradicals, e.g., tetramethylpiperidinyl-N-oxyradical (TEMPO), substituted catechols, e.g., t-butylcatechol, amines, e.g., phenothiazine, diphenylamine, and phenyl-β-naphthylamine, nitrosobenzene, picric acid, molecular oxygen, sulfur, and copper(II) chloride. Among them, hydroquinones, phenothiazine, and N-oxyradicals can be employed from the viewpoint of versatility and inhibition of polymerization.

The lower limit of usage of the polymerization inhibitor is usually 10 ppm or more, and preferably 50 ppm or more relative to the above-described (meth)acrylate compound. The upper limit is usually 10,000 ppm or less, and preferably 1,000 ppm or less. In the case where the usage is too small, the effect of the polymerization inhibitor is not exerted or the effect is small, and there is a risk of proceeding of polymerization during reaction or during concentration in an after-treatment step. In the case where the usage is too large, for example, the inhibitor serves as an impurity in production of an optical material described later, and unfavorably, there is a risk of exerting adverse influences, e.g., inhibition of the polymerization reactivity.

Next, the features of the optical material organic compound according to the present invention will be described.

The present inventors noted that in order to give a chromatic aberration correction function higher than ever to an optical element, satisfaction of the following items (i) and (ii) by the material characteristics of the optical element was very effective in optical design.

(i) The transmittance in the visible light region is high (ii) The secondary dispersion characteristic (θg,F) is out of those of common materials and is a larger characteristic (high θg,F characteristic)

Specifically, the area B shown in FIG. 1 is mentioned, wherein the relationship between the Abbe number ($\nu_d$) and the secondary dispersion characteristic (θg,F) is out of the plots with respect to glass materials or common organic resin materials. As for the specific characteristic, the 500 μm internal transmittance is 90% or more at 410 nm. The characteristic of the area B is $\nu_d<25$ and θg,F>0.70.

The present inventors performed intensive research on the materials satisfying the characteristics within the area B shown in FIG. 1. As a result, it was found that an aromatic compound having a long conjugated structure including at least one each of electron-withdrawing substituent and electron-donating substituent, which can be conjugated, served as a material having both the characteristics that the dispersion characteristic (Abbe number ($\nu_d$)) of the refractive index was high, the secondary dispersion characteristic (θg,F) was high (high θg,F characteristic), and the chromatic aberration correction function delivered high performance and the practicality. That is, the present inventors found a compound having the partial structure represented by the following the following general formula (1A) or (2A) as a basic structure.

(1A)

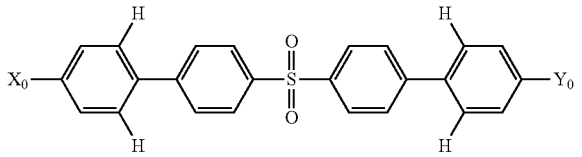

(2A)

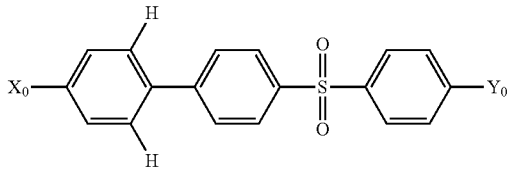

In general, regarding the compound having a long conjugated structure typified by an aromatic compound, the band gap is smaller than that of a common material and, thereby, an absorption edge in the ultraviolet region is shifted to the visible light region side. Under the influence thereof, the compound having a long conjugated structure exhibits a high-refractive index characteristic. This high-refractive index characteristic exerts a greater influence on the small wavelength side and, inevitably, the secondary dispersion characteristic (θg,F) increases so that the characteristics of the compound fall in the area B shown in FIG. 1. However, a practical material is not obtained by merely simply coupling aromatic compounds so as to form a long conjugated structure. For example, a large aromatic compound has remaining problems in synthetic property, compatibility with other compounds, and coloring. Therefore, an aromatic compound having a long conjugated structure including at least one each of electron-withdrawing substituent and electron-donating substituent, which can be conjugated, is desirable.

As described above, from the viewpoint of improvement of the refractive index characteristic and the secondary dispersion characteristic, it is favorable that the conjugation length of the compound is maximized. However, if the conjugated structure becomes too long, the transmittance is reduced in the small wavelength side of the visible light region. Therefore, in the case of use as an optical material, it is necessary that the length of the conjugated structure is adjusted. In this regard, the partial structures represented by the general formulae (1A) and (2A) have conjugation lengths suitable for the transmittance and the refractive index characteristic.

Meanwhile, examples of electron-withdrawing substituents, which can be conjugated, include sulfone, ketone, imine, oxime, nitrile, nitro, and ester. In consideration of long-term stability of products, sulfone, ketone, nitrile, and ester are mentioned and, in particular, sulfone is mentioned. The compound represented by the general formula (1A) or (2A) includes sulfone as a partial structure.

Examples of electron-donating substituents, which can be conjugated, include a hydroxyl group, a mercapto group, an alkoxy group, an alkylthio group, an alkyl group, an amino group, an alkylamino group, a dialkylamino group, and a carbonyloxy group. In particular, a hydroxyl group, a mercapto group, an alkoxy group, an alkylthio group, an alkyl group, and a carbonyloxy group can be mentioned. However, if the molecular weight of the substituent is too large, a high secondary dispersion characteristic (θg,F) is not obtained. Consequently, the substituent is desirably a substituent having the carbon number of 0 to 10. From the viewpoint of ease of synthesis, the substituent can have the carbon number of 1 to 4. In the present invention, in particular, a hydroxyl group, a mercapto group, an alkoxy group having the carbon number of 1 to 4, and an alkylthio group having the carbon number of 1 to 4 can be selected as the substituents.

Furthermore, H (hydrogen atom) shown in the general formulae (1) and (2) is necessary for adjusting the conjugated structure. Regarding other substituents, in some cases, the characteristics are not manifested because conjugation is broken due to torsion of aromatic rings resulting from steric hindrance of the substituent concerned.

Next, the optical material according to the present invention will be described.

The optical materials according to the present invention are roughly divided into the following items (A) to (C).

(A) A material prepared by containing the optical material organic compound according to the present invention into a matrix polymer (B) A material prepared by polymerizing the optical material organic compound according to the present invention (C) A material prepared by copolymerizing the optical material organic compound according to the present invention and another compound Among the optical material organic compounds according to the present invention, compounds not having a (meth) acryloyl group are used in the form (A). Meanwhile, among the optical material organic compounds according to the present invention, compounds having a (meth)acryloyl group can be used in any one of the forms (A) to (C), although merely the form (B) or the form (C) is employed.

In the case where the optical material organic compound according to the present invention is used in the form (A), examples of matrix polymers include (meth)acrylic polymers; allyl based polymers; polyolefin based resins, such as, ethylene homopolymers, random or block copolymers of ethylene and at least one type of α-olefin, e.g., propylene, 1-butene, 1-pentene, 1-hexene, and 4-methyl-1-pentene, random or block copolymers of ethylene and at least one type of vinyl acetate, acrylic acid, methacrylic acid, methyl acrylate, or methyl methacrylate, propylene homopolymers, random or block copolymers of propylene and at least one type of α-olefin, e.g., 1-butene, 1-pentene, 1-hexene, and 4-methyl-1-pentene, other than propylene, 1-butene homopolymers, ionomer resins, and mixtures of these polymers; hydrocarbon based resins, e.g., petroleum resins and terpene resins; polyester based resins, e.g., polyethylene terephthalate, polybutylene terephthalate, and polyethylene naphthalate; polyamide based resins, e.g., nylon 6, nylon 66, nylon 11, nylon 12, nylon 610, nylon 6/66, nylon 66/610, and nylon MXD; acrylic resins, e.g., polymethyl methacrylate; styrene and acrylonitrile based resins, e.g., polystyrene, styrene-acrylonitrile copolymers, styrene-acrylonitrile-butadiene copolymers, and polyacrylonitrile; polyvinyl alcohol based resins, e.g., polyvinyl alcohol and ethylene-vinyl alcohol copolymers; polycarbonate resins; polyketone resins; polymethylene oxide resins; polysulfone resins; polyimide resins; and polyamide imide resins. In this regard, the (meth)acrylic polymer refers to a polymer prepared by polymerizing a (meth)acrylate compound described later. The allyl based polymer refers to a polymer prepared by polymerizing an allyl compound described later. One type of these resins may be used alone or at least two types may be used in combination. These matrix polymers are selected appropriately in consideration of the compatibility with the optical material organic compound according to the present invention.

In the case where the optical material organic compound according to the present invention is used in the form (A), the content of the optical material organic compound according to the present invention relative to the whole materials is selected appropriately in consideration of the compatibility between the optical material organic compound according to the present invention and the matrix polymer.

In the case where the optical material organic compound according to the present invention is used in the form (A), the content of the resin serving as the matrix polymer is 50 percent by weight or more, and 99 percent by weight or less relative to the whole materials. It is desirable that the content is 50 percent by weight or more, and 80 percent by weight or less in consideration of the θg,F characteristic of the resulting optical material and the brittleness of a molded body.

In the case where the optical material organic compound according to the present invention is used in the form (B), the optical material according to the present invention is produced from a composition including the optical material organic compound according to the present invention ((meth)acrylate compound) and a polymerization initiator. This composition may further contain, a polymerization inhibitor, a photosensitizer, a resin, and the like, as necessary.

Examples of polymerization initiators includes agents which generate radical species or cationic species through light irradiation and agents which generate radical species through heat, although not limited to them.

Examples of polymerization initiators which generate radical species through light irradiation include 2-benzyl-2-dimethylamino-1-(4-morpholinophenyl)-1-butanone, 1-hydroxy-cyclohexyl-phenyl ketone, 2-hydroxy-2-methyl-1-phenyl-propan-1-one, bis(2,4,6-trimethylbenzoyl) phenylphosphine oxide, 4-phenylbenzophenone, 4-phenoxybenzophenone, 4,4'-diphenylbenzophenone, and 4,4'-diphenoxybenzophenone, although not limited to them.

As for the polymerization initiators which generate cationic species through light irradiation, iodonium(4-methylphenyl)[4-(2-methylpropyl)phenyl]-hexafluoro phosphate is mentioned as a favorable polymerization initiator, although not limited to this.

Examples of polymerization initiators which generate radical species through heat include azo compounds, e.g., azobisisobutyronitrile (AIBN), and peroxides, e.g., benzoyl peroxide, t-butyl peroxypivalate, t-butyl peroxyneohexanoate, t-hexyl peroxyneohexanoate, t-butyl peroxyneodecanoate, t-hexyl peroxyneodecanoate, cumyl peroxyneohexanoate, and cumyl peroxyneodecanoate, although not limited to them.

In the case where the optical material organic compound according to the present invention is used in the form (B), the content of the optical material organic compound according to the present invention is desirably 1.0 percent by weight or more, and 99 percent by weight or less, and preferably 50 percent by weight or more, and 99 percent by weight or less.

Regarding the optical material according to the present invention, in the case where the optical material organic compound according to the present invention is used in the form (B), the quantity of addition of the photopolymerization initiator used for curing and molding of the optical material according to the present invention is preferably within the range of 0.01 percent by weight or more, and 10.00 percent by weight or less relative to a polymerizable component. One type of the photopolymerization initiator may be used alone or at least two types may be used in combination in accordance with the reactivity of the resin and the wavelength of light irradiation.

Regarding the optical material according to the present invention, in the case where the optical material organic compound according to the present invention is used in the form (B), the polymerization initiator described above as a preservative of the optical material organic compound according to the present invention is mentioned as the polymerization initiator used.

In the case where polymerization is initiated by applying ultraviolet rays or the like as light, a sensitizer or the like in the related art may also be used. Typical examples of sensitizers include benzophenone, 4,4-diethylaminobenzophenone, 1-hydroxycyclohexyl phenyl ketone, isoamyl p-dimethylaminobenzoate, methyl 4-dimethylaminobenzoate, benzoin, benzoin ethyl ether, benzoin isobutyl ether, benzoin isopropyl ether, 2,2-diethoxyacetophenone, methyl o-benzoylbenzoate, 2-hydroxy-2-methyl-1-phenylpropan-1-one, and acylphosphine oxide.

The ratio of addition of the photopolymerization initiator relative to the polymerizable resin component can be selected appropriately in accordance with the quantity of light irradiation and an additive heating temperature. The adjustment can also be performed in accordance with the desired average molecular weight of the resulting polymer.

The quantity of addition of the photopolymerization initiator used for curing and molding of the optical material according to the present invention is preferably within the range of 0.01 percent by weight or more, and 10.00 percent by weight or less relative to the polymerizable component. One type of the photopolymerization initiator may be used alone or at least two types may be used in combination in accordance with the reactivity of the resin and the wavelength of light irradiation.

In the case where the optical material organic compound according to the present invention is used in the form (C), a compound subjected to copolymerization with the optical material organic compound according to the present invention is not specifically limited. Examples thereof include (meth)acrylate compounds, e.g., 1,3-adamantanediol dimethacrylate, 1,3-adamantanedimethanol dimethacrylate, tricyclodecane dimethanol diacrylate, pentaerithritol tetraacrylate, propoxylated neopentyl glycol diacrylate, dipropylene glycol diacrylate, ethoxylated bisphenol A dimethacrylate, tris(2-hydroxyethyl)isocyanurate triacrylate, 2(2-ethoxyethoxy)ethyl acrylate, stearyl acrylate, tetrahydrofurfuryl acrylate, 2-phenoxyethyl acrylate, isodecyl acrylate, isobonyl acrylate, isobonyl methacrylate, 1,3-butylene glycol diacrylate, 1,4-butanediol diacrylate, diethylene glycol diacrylate, 1,6-hexanediol diacrylate, triethylene glycol diacrylate, tripropylene glycol diacrylate, dipropylene glycol diacrylate, triethylene glycol dimethacrylate, ethylene glycol dimethacrylate, tetraethylene glycol dimethacrylate, 1,4-butanediol dimethacrylate, diethylene glycol dimethacrylate, 1,6-hexanediol dimethacrylate, tripropylene glycol dimethacrylate, dipropylene glycol dimethacrylate, trimethylolpropane trimethacrylate, 9,9-bis[4-(2-acryloyloxyethoxy)phenyl]fluorene, 9,9-bis[4-(2-methacryloyloxyethoxy)phenyl]fluorene, 9,9-bis[4-(2-acryloyloxy)phenyl]fluorene, 9,9-bis[4-(2-methacryloyloxy)phenyl]fluorene, benzyl acrylate, benzyl methacrylate, butoxyethyl acrylate, butoxymethyl methacrylate, cyclohexyl acrylate, cyclohexyl methacrylate, 2-hydroxyethyl acrylate, 2-hydroxymethyl methacrylate, glycidyl acrylate, glycidyl methacrylate, phenoxyethyl acrylate, phenoxyethyl methacrylate, phenyl methacrylate, ethylene glycol diacrylate, ethylene glycol dimethacrylate, diethylene glycol diacrylate, diethylene glycol dimethacrylate, triethylene glycol diacrylate, triethylene glycol dimethacrylate, tetraethylene glycol diacrylate, tetraethylene glycol dimethacrylate, polyethylene glycol dimethacrylate, polyethylene glycol diacrylate, neopentyl glycol diacrylate, neopentyl glycol dimethacrylate, ethylene glycol bisglycidyl acrylate, ethylene glycol bisglycidyl methacrylate, bisphenol A diacrylate, bisphenol A dimethacrylate, 2,2-bis(4-acryloxyethoxy phenyl)propane, 2,2-bis(4-methacryloxyethoxy phenyl)propane, 2,2-bis(4-acryloxydiethoxy phenyl)propane, 2,2-bis(4-methacryloxydiethoxy phenyl)propane, bisphenol F diacrylate, bisphenol F dimethacrylate, 1,1-bis(4-acryloxyethoxy phenyl)methane, 1,1-bis(4-methacryloxyethoxy phenyl)methane, 1,1-bis(4-acryloxydiethoxy phenyl)methane, 1,1-bis(4-acryloxyethoxy phenyl)sulfone, 1,1-bis(4-acryloxyethoxy phenyl)sulfone, 1,1-bis(4-methacryloxyethoxy phenyl)sulfone, 1,1-bis(4-acryloxydiethoxy phenyl)sulfone, 1,1-bis(4-methacryloxydiethoxy phenyl)sulfone, dimethyloltricyclodecane diacrylate, trimethylolpropane triacrylate, trimethylolpropane trimethacrylate, glycerol diacrylate, glycerol dimethacrylate, pentaerithritol triacrylate, pentaerithritol tetraacrylate, pentaerithritol tetramethacrylate, methylthio acrylate, methylthio methacrylate, phenylthio acrylate, benzylthio methacrylate, xylylenedithiol diacrylate, xylylenedithiol dimethacrylate, mercaptoethylsulfide diacrylate, and mercaptoethylsulfide dimethacrylate, allyl compounds, e.g., allyl glycidyl ether, diallyl phthalate, diallyl terephthalate, diallyl isophthalate, diallyl carbonate, and diethylene glycol bisallyl carbonate, vinyl compounds, e.g., styrene, chlorostyrene, methylstyrene, bromostyrene, dibromostyrene, divinyl benzene, and 3,9-divinylspirobi(m-dioxane), and diisopropenyl benzene. However, the present invention is not limited to them.

The above-described resin may be a thermoplastic resin. Examples thereof include polyolefin based resins, such as, ethylene homopolymers, random or block copolymers of ethylene and at least one type of α-olefin, e.g., propylene, 1-butene, 1-pentene, 1-hexene, and 4-methyl-1-pentene, random or block copolymers of ethylene and at least one type of vinyl acetate, acrylic acid, methacrylic acid, methyl acrylate, or methyl methacrylate, propylene homopolymers, random or block copolymers of propylene and at least one type of α-olefin, e.g., 1-butene, 1-pentene, 1-hexene, and 4-methyl-1-pentene, other than propylene, 1-butene homopolymers, ionomer resins, and mixtures of these polymers; hydrocarbon based resins, e.g., petroleum resins and terpene resins; polyester based resins, e.g., polyethylene terephthalate, polybutylene terephthalate, and polyethylene naphthalate; polyamide based resins, e.g., nylon 6, nylon 66, nylon 11, nylon 12, nylon 610, nylon 6/66, nylon 66/610, and nylon MXD; acrylic resins, e.g., polymethyl methacrylate; styrene and acrylonitrile based resins, e.g., polystyrene, styrene-acrylonitrile copolymers, styrene-acrylonitrile-butadiene copolymers, and polyacrylonitrile; polyvinyl alcohol based resins, e.g., polyvinyl alcohol and ethylene-vinyl alcohol copolymers; polycarbonate resins; polyketone resins; polymethylene oxide resins; polysulfone resins; polyimide resins; and polyamide imide resins. One type of these resins may be used alone or at least two types may be used in combination.

In the case where the optical material organic compound according to the present invention is used in the form (C), the content of the compound copolymerized with the optical material organic compound according to the present invention is 1.0 percent by weight or more, and 80 percent by weight or less relative to the whole materials. The content is preferably 1.0 percent by weight or more, and 30 percent by weight or less in consideration of the θg,F characteristic of the resulting optical material and the brittleness of a molded body.

Figure 2A:
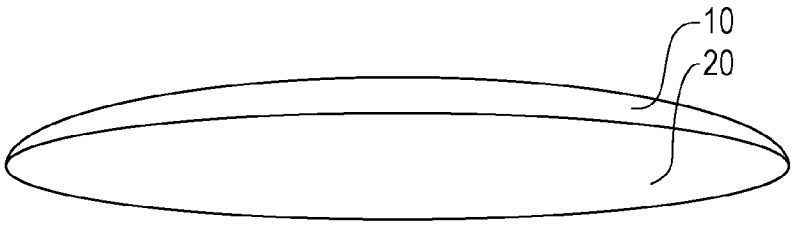
FIGS. 2A and 2B are schematic diagrams showing examples of the optical element according to the present invention.
Figure 2B:
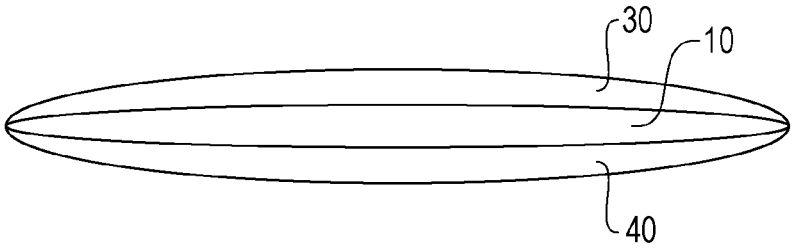

Next, the optical element according to the present invention will be described with reference to the drawings. FIGS. 2A and 2B are schematic diagrams showing examples of the optical element according to the present invention. Regarding the optical element shown in FIG. 2A, a thin film (optical member 10) prepared by molding the optical material according to the present invention is disposed on one surface of a lens substrate 20. As for a method for producing the optical element shown in FIG. 2A, for example, a method in which a layer structure having a small film thickness is formed on a substrate composed of a light-transmitting material is adopted. Specifically, a mold formed from a metal material is disposed at a predetermined distance from a glass substrate, and molding is performed by filling a fluid optical material or optical resin composition into a gap between the mold and the glass substrate and pressing lightly. Then, the optical material or the optical resin composition is polymerized while that state is maintained, as necessary. The light irradiation for the above-described polymerization reaction is performed by using light, usually ultraviolet rays or visible light, with a wavelength suitable for a mechanism resulting from radical generation by using a photopolymerization initiator. For example, the molded material, e.g., a monomer for preparation of an optical material, is irradiated with light uniformly through a light-transmitting material used as the above-described substrate, specifically a glass substrate. The quantity of light irradiation is selected appropriately in accordance with the mechanism resulting from radical generation by using a photopolymerization initiator and the content of the photopolymerization initiator contained.

In production of a molded body of the optical material through the above-described photopolymerization reaction, it is advantageous that the light is uniformly applied to the whole raw materials, e.g., a monomer, in a mold for molding. Therefore, the light with a wavelength capable of performing uniform light irradiation through the light-transmitting material used for the substrate, e.g., a glass substrate, can be selected. At this time, it is more favorable that the thickness of the molded body of the optical material disposed on the substrate composed of a light-transmitting material is reduced.

Meanwhile, regarding the optical element shown in FIG. 2B, a thin film (optical member 10) prepared by molding the optical material according to the present invention is disposed between a lens substrate 30 and a lens substrate 40. As for a method for producing the optical element shown in FIG. 2B, for example, molding is performed by pouring an uncured resin composition, which is the same as that described above, or the like between the surface in the resin composition side of the above-described molded body and another lens substrate opposite thereto and pressing lightly. Then, the uncured resin composition is photopolymerized while this state is maintained. In this manner, a molded body in which the above-described optical material is sandwiched between lenses can be obtained.

Likewise, a molded body can be produced by a heat polymerization method. In this case, it is desirable that the temperature of the whole is made more uniform. Regarding the present invention, it is more favorable that the total thickness of the molded body, which is disposed on the substrate of a light-transmitting material, of a polymerizable composition is reduced. In the case where the total thickness of the resulting molded body of the optical material is increased, it is necessary that the quantity of irradiation, the irradiation intensity, the light source, and the like are selected in further consideration of film thickness, absorption of the resin component, and absorption of fine particle component.

In the case where the molded body of the optical material containing the optical material organic compound according to the present invention is formed, the molding method is not specifically limited, although melt molding can be particularly employed in order to obtain a molded body excellent in characteristics, e.g., the low birefringence, the mechanical strength, and dimensional accuracy. Examples of the melt molding method include press molding, extrusion, and injection molding, although injection molding can be employed from the viewpoint of the moldability and the productivity. The molding condition in a molding step is selected appropriately in accordance with the purpose of use or a molding method, although the temperature of the resin composition in the injection molding is preferably within the range of 150° C. to 400° C., more preferably within the range of 200° C. to 350° C., and particularly preferably within the range of 200° C. to 330° C. Molding within the above-described temperature range can give appropriate fluidity to the resin in the molding so as to prevent occurrences of sink mark and strain of the molded body and an occurrence of silver streak due to thermal decomposition of the resin and, furthermore, can prevent yellowing of the molded body effectively.

The molded body produced from the optical material according to the present invention by the above-described molding method can be used as an optical element. Examples of uses of the optical element include camera lenses.

EXAMPLES

The present invention will be described below in further detail with reference to examples. However, the present invention is not limited to the examples described below within the bounds of not exceeding the gist thereof. Individual abbreviations in reaction formulae represent the following. The molecular structure of synthesized compounds were analyzed by using JNM-ECA400 NMR produced by JEOL LTD.

THF: tetrahydrofuran

DMF: N,N'-dimethylformamide

TsOH: paratoluenesulfonic acid hydrate

Synthesis Example 1

Synthesis of 4,4'-bis(4-hydroxyphenyl)diphenyl sulfone

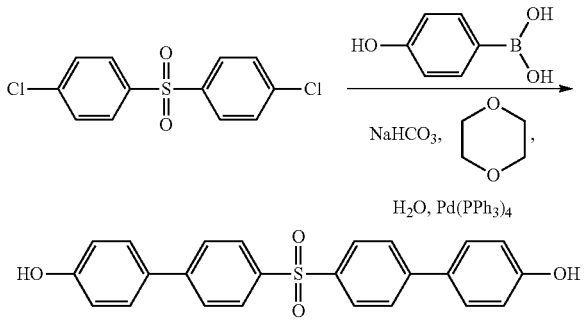

(Intermediate compound D1)

The following reagents and solvents were put into a reaction container.

4,4'-dichlorodiphenyl sulfone: 15 g
4-hydroxyphenylboric acid: 21 g
sodium hydrogen carbonate: 33 g
1,4-dioxane: 500 ml
water: 250 ml
tetrakistriphenylphosphine palladium: 2.5 g Subsequently, the reaction solution was heated to 90° C. and agitation was performed at this temperature (90° C.) for 20 hours. At this time, the degree of proceeding of the reaction was ascertained with thin layer chromatography (hereafter referred to as TLC) appropriately. After the reaction was completed, the reaction solution was diluted with water. Thereafter, an organic phase was recovered through solvent extraction. The resulting organic phase was washed with water and saturated saline solution in that order and was dried with anhydrous magnesium sulfate. Then, a residue obtained by concentration of the organic phase under reduced pressure was subjected to recrystallization with a mixed solution of hexane and ethyl acetate, so that 20 g (yield 95%) of light yellow crystal of 4,4'-bis(4-hydroxyphenyl)diphenyl sulfone (hereafter referred to as Intermediate compound D1) was obtained.

Synthesis Example 2

Synthesis of
4-(2-tetrahydropyranyloxyethylthio)-phenylboric acid pinacol ester

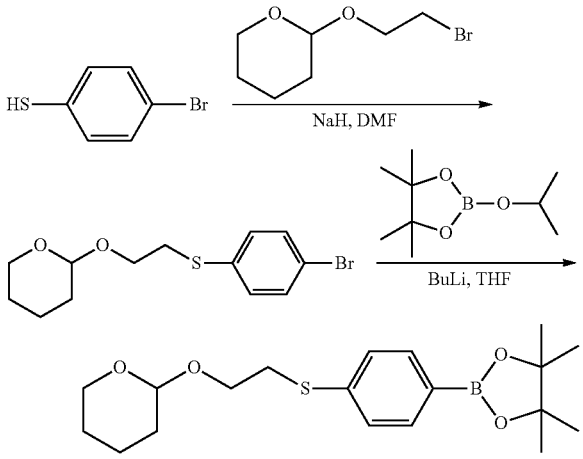

(Intermediate compound D2)

(1) The following reagent and solvent were put into a reaction container.

sodium hydride (55%): 6.2 g
N,N-dimethylformamide: 200 ml

After the reaction solution was cooled to 0° C., 25 g of 4-bromothiophenol was added gradually. Subsequently, the reaction solution was agitated while the temperature was raised to room temperature. After 24 ml of 2-(2-bromoethoxy)tetrahydro-2H-pyran was added, the temperature of the reaction solution was raised to 40° C., and agitation was performed at this temperature (40° C.) for 12 hours. At this time, the degree of proceeding of the reaction was ascertained with TLC appropriately. Then, the reaction was terminated with water, and an organic phase was extracted with ethyl acetate. The resulting organic phase was washed with water and saturated saline solution in that order and was dried with anhydrous magnesium sulfate. A crude product obtained by concentrating the organic phase under reduced pressure was refined through column chromatography, so that 44 g of 4-(2-tetrahydropyranyloxyethylthio)-bromobenzene was obtained. The resulting compound was used as-is in the following step.

(2) The compound obtained in the item (1) and 400 ml of tetrahydrofuran were put into a reaction container. After the reaction solution was cooled to −78° C., 64 ml of butyl lithium (2.6 M) was dropped gradually. Subsequently, the reaction solution was agitated at the same temperature (−78° C.) for further 2 hours. After 35 ml of 2-isopropoxy-4,4,5,5-tetramethyl-1,3,2-dioxaborolane was dropped, the reaction solution was agitated for 12 hours while the temperature was raised to room temperature gradually. At this time, the degree of proceeding of the reaction was ascertained with TLC appropriately. Then, the reaction was terminated with an ammonium chloride aqueous solution, and an organic phase was extracted with ethyl acetate. The resulting organic phase was washed with water and saturated saline solution in that order and was dried with anhydrous magnesium sulfate. A crude product obtained by concentrating the organic phase under reduced pressure was refined through column chromatography, so that 31 g (yield 64%) of 4-(2-tetrahydropyranyloxyethylthio)-phenylboric acid pinacol ester (hereafter referred to as Intermediate compound D2) was obtained.

Synthesis Example 3

Synthesis of 4-(4-hydroxyphenylsulfonyl)phenyl trifluoromethanesulfonate

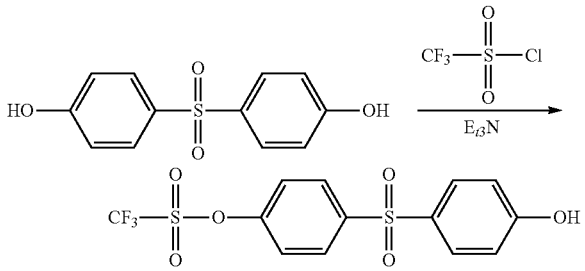

(Intermediate compound D3)

The following reagents and solvent were put into a reaction container.

4,4'-dihydroxydiphenyl sulfone: 25 g
trifluoromethanesulfonyl chloride: 12 ml
chloroform: 200 ml After the reaction solution was cooled to 0° C., 15 ml of trimethylamine was dropped gradually. Subsequently, the reaction solution was agitated at the same temperature (0° C.) for 1 hour. Thereafter, the temperature of the reaction solution was raised to room temperature and agitation was performed for further 5 hours. At this time, the degree of proceeding of the reaction was ascertained with TLC appropriately. Then, the reaction was terminated with an ammonium chloride aqueous solution, and an organic phase was extracted with ethyl acetate. The resulting organic phase was washed with water and saturated saline solution in that order and was dried with anhydrous magnesium sulfate. A crude product obtained by concentrating the organic phase under reduced pressure was refined through column chromatography, so that 17 g (yield 45%) of 4-(4-hydroxyphenylsulfonyl)phenyl trifluoromethanesulfonate (hereafter referred to as Intermediate compound D3) was obtained.

Synthesis Example 4

Synthesis of 4,4'-bis(3-hydroxymethyl-4-methoxyphenyl)diphenyl sulfone

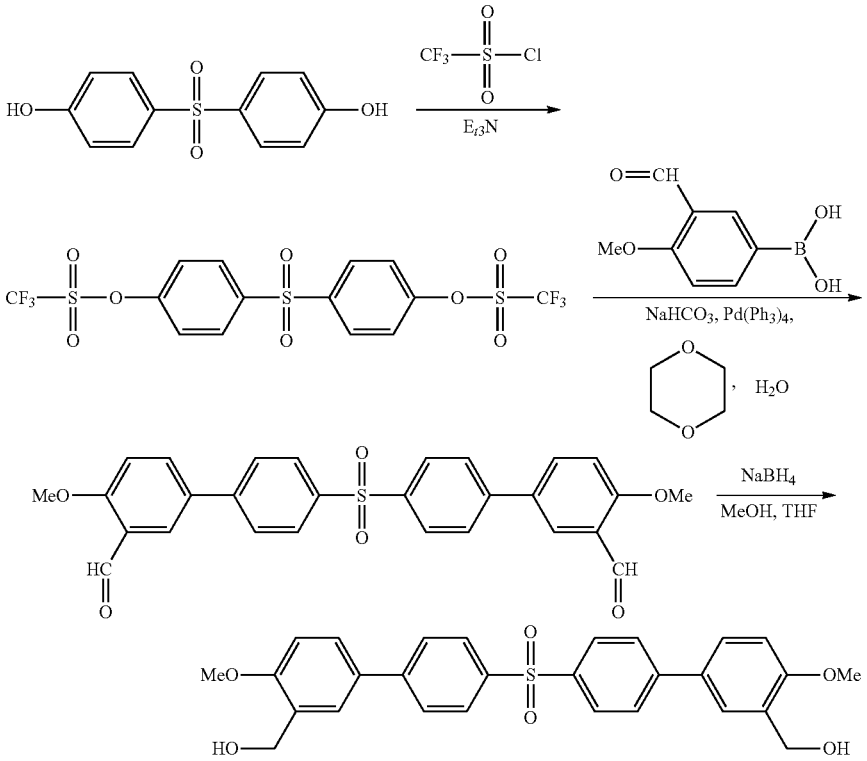

(Intermediate compound D4)

(1) The following reagents and solvent were put into a reaction container.

4,4'-dihydroxydiphenyl sulfone: 25 g trifluoromethanesulfonyl chloride: 25 ml chloroform: 300 ml After the reaction solution was cooled to 0° C., 42 ml of trimethylamine was dropped gradually. Subsequently, the reaction solution was agitated at the same temperature (0° C.) for 1 hour. Thereafter, the temperature of the reaction solution was raised to room temperature and agitation was performed for further 5 hours. At this time, the degree of proceeding of the reaction was ascertained with TLC appropriately. Then, the reaction was terminated with an ammonium chloride aqueous solution, and an organic phase was extracted with ethyl acetate. The resulting organic phase was washed with water and saturated saline solution in that order and was dried with anhydrous magnesium sulfate. A crude product obtained by concentrating the organic phase under reduced pressure was subjected to recrystallization with a hexane/ethyl acetate mixed solution, so that 49 g (yield 94%) of diphenylsulfon-4,4'-diylbis(trifluoromethane sulfonate) was obtained. The resulting compound was used as-is in the following step.

(2) The following reagents and solvents were put into a reaction container.

diphenylsulfon-4,4'-diylbis(trifluoromethane sulfonate (the compound synthesized in the item (1) was used as-is): 28 g 3-formyl-4-methoxyphenylboric acid: 25 g sodium hydrogen carbonate: 30 g tetrakistriphenylphosphine palladium: 1.3 g 1,4-dioxane: 500 ml water: 250 ml Subsequently, the reaction solution was heated to 80° C. and agitation was performed at this temperature (80° C.) for 3 hours. At this time, the degree of proceeding of the reaction was ascertained with TLC appropriately. After 250 ml of water was added, the reaction solution was agitated at 80° C. for 1 hour. Thereafter, the resulting crystal (crude crystal) was filtrated and recovered. The resulting crude crystal was washed with ethanol and was subjected to recrystallization with a hexane/ethyl acetate mixed solvent, so that a light gray crystal was obtained.

Then, the resulting light gray crystal and solvents described below were put into a reaction container.

methanol: 200 ml tetrahydrofuran: 200 ml

After the reaction solution was cooled to 0° C., 12 g of sodium borohydride was added gradually. Subsequently, the reaction solution was agitated at the same temperature (0° C.) while the degree of proceeding of the reaction was ascertained with TLC. After proceeding of the reaction was ascertained, 2 N hydrochloric acid aqueous solution was added. Then, the reaction solution was agitated at room temperature for 1 hour. A generated crystal was washed with sodium hydrogen carbonate aqueous solution and water in that order. Subsequently, recrystallization with an ethanol/ethyl acetate/hexane mixed solvent was performed, so that 48 g (yield 90%) of 4,4'-bis(3-hydroxymethyl-4-methoxyphenyl)diphenyl sulfone (hereafter referred to as Intermediate compound D4) was obtained.

Example 1

The synthesis scheme of a compound synthesized in Example 1 will be described below. Furthermore, a specific synthesis method will be explained below.

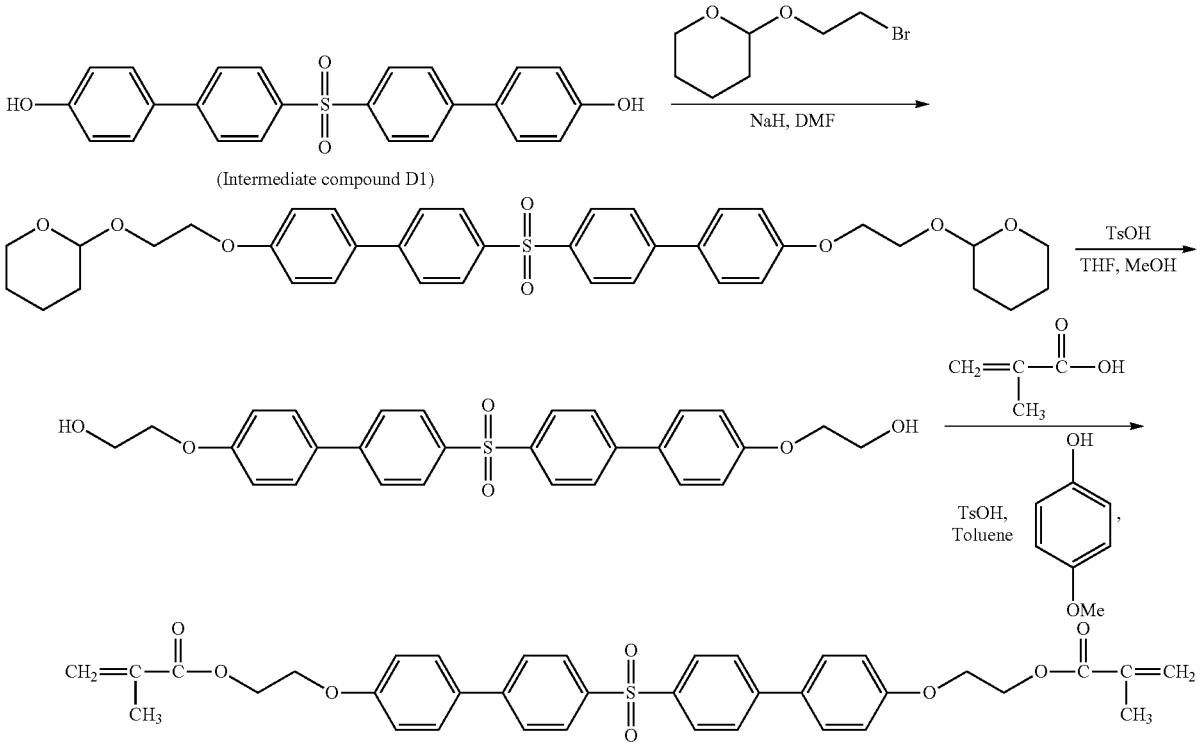

(1) The following reagent and solvent were put into a reaction container.

sodium hydride (55%): 620 mg

N,N-dimethylformamide: 30 ml

After the reaction solution was cooled to 0° C., Intermediate compound D1 (2.3 g) was added gradually. Subsequently, the reaction solution was agitated while the temperature was raised to room temperature. Then, 2.7 ml of 2-(2-bromoethoxy)tetrahydro-2H-pyran was added, the reaction solution was heated to 60° C., and agitation was performed at this temperature (60° C.) for 12 hours. At this time, the degree of proceeding of the reaction was ascertained with TLC appropriately. Thereafter, the reaction was terminated with water, and an organic phase was extracted with ethyl acetate. The resulting organic phase was washed with water and saturated saline solution in that order and was dried with anhydrous magnesium sulfate. The organic phase was concentrated under reduced pressure so as to obtain a crude product. The thus obtained crude product was used as-is in the following step.

(2) The crude product obtained in the item (1) and the following reagent and solvents were put into a reaction container.

tetrahydrofuran: 10 ml methanol: 40 ml paratoluenesulfonic acid hydrate: a small amount Subsequently, the reaction solution was agitated at room temperature for 12 hours. The degree of proceeding of the reaction was ascertained with TLC appropriately. Then, generated precipitates were filtrated, and the precipitates were subjected to recrystallization with a chloroform/hexane mixed solution, so that 2.3 g (yield 82%) of 4,4'-bis(4-(2-hydroxyethoxy)phenyl)diphenyl sulfone was obtained.

(3) The following reagents and solvent were put into a reaction container.

4,4'-bis(4-(2-hydroxyethoxy)phenyl)diphenyl sulfone: 3.0 g methacrylic acid: 30 ml paratoluenesulfonic acid: 0.2 g 4-methoxyphenol: 0.2 g toluene: 30 ml Then, the reaction solution was heated and agitated for 20 hours. At this time, generated water was removed appropriately, and the degree of proceeding of the reaction was ascertained with TLC appropriately. The reaction solution was neutralized by adding a sodium hydroxide aqueous solution, and an organic phase was extracted with chloroform. The resulting organic phase was washed with water and saturated saline solution in that order and was dried with anhydrous magnesium sulfate. Next, a crude product obtained by concentrating the organic phase under reduced pressure was refined through column chromatography, so that 2.1 g (yield 55%) of 4,4'-bis(4-(2-methacryloyloxyethoxy)phenyl)diphenyl sulfone was obtained.

The structure of the resulting compound was ascertained with $^{1}$H-NMR.

$^1$H-NMR ($CDCl_3$; TMS): δ 1.95 (s, 6H), 4.27 (t, 4H), 4.52 (t, 4H), 5.59 (s, 2H), 6.14 (s, 2H), 6.99-7.01 (m, 4H), 7.25-7.26 (m, 4H), 7.50-7.53 (m, 4H), 7.65-7.67 (m, 4H), 7.98-8.02 (m, 4H)

Example 2

The synthesis scheme of a compound synthesized in Example 1 will be described below. Furthermore, a specific synthesis method will be explained below.

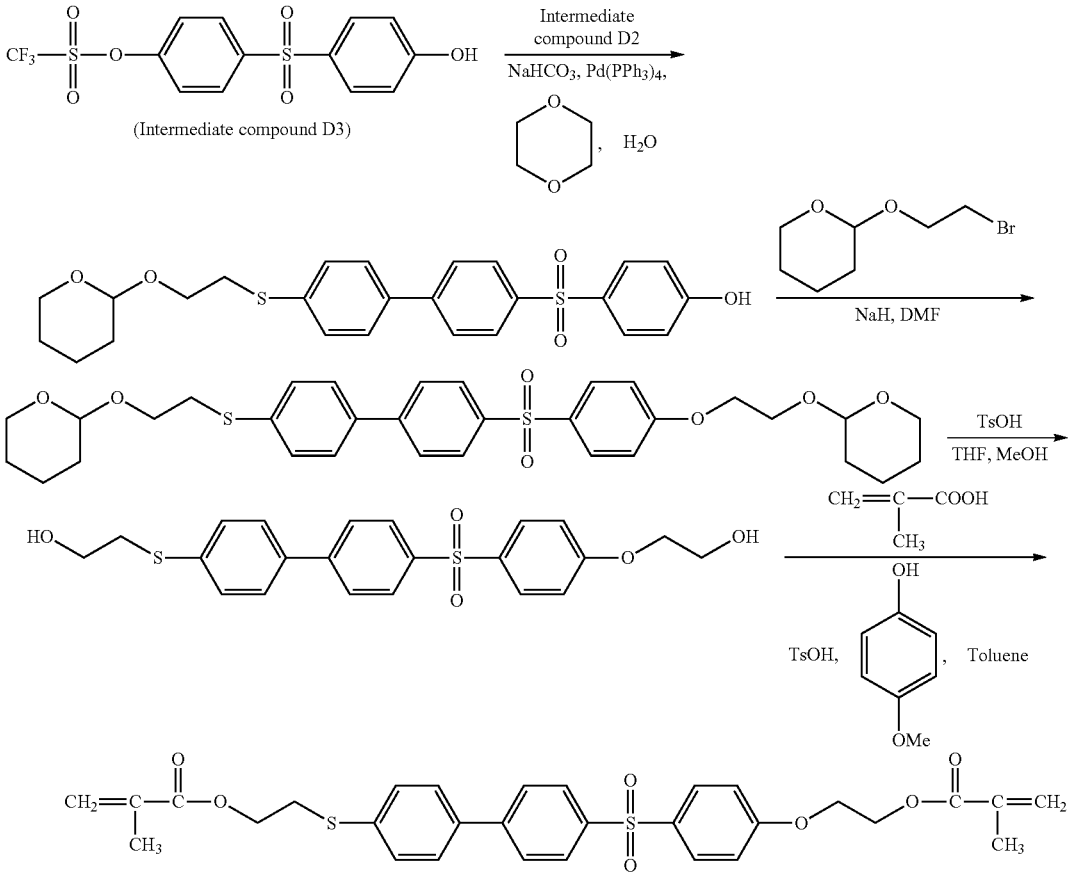

(1) The following reagents and solvents were put into a reaction container.

Intermediate compound D3: 5 g
Intermediate compound D2: 6 g
sodium hydrogen carbonate: 4 g
dioxane: 150 ml
water: 70 ml
tetrakistriphenylphosphine palladium: 0.3 g Subsequently, the reaction solution was heated to 90° C. and agitation was performed at this temperature (90° C.) for 20 hours. At this time, the degree of proceeding of the reaction was ascertained with TLC appropriately. Then, the reaction was terminated with an ammonium chloride aqueous solution, and an organic phase was extracted with ethyl acetate. The resulting organic phase was washed with water and saturated saline solution in that order and was dried with anhydrous magnesium sulfate. A crude product obtained by concentrating the organic phase under reduced pressure was refined through column chromatography. The compound obtained through this refining was used as-is in the following step.

(2) The following reagent and solvent were put into a reaction container.

sodium hydride: 0.6 g
N,N-dimethylformamide: 100 ml

After the reaction solution was cooled to 0° C., the compound obtained in the item (1) was added gradually. Subsequently, the reaction solution was agitated for 2 hours while the temperature was raised to room temperature. Then, 2.4 ml of 2-(2-bromoethoxy)tetrahydro-2H-pyran was added, the reaction solution was heated to 60° C., and agitation was performed at this temperature (60° C.) for 10 hours. At this time, the degree of proceeding of the reaction was ascertained with TLC appropriately. Thereafter, the reaction was terminated with an ammonium chloride aqueous solution, and an organic phase was extracted with ethyl acetate. The resulting organic phase was washed with water and saturated saline solution in that order and was dried with anhydrous magnesium sulfate. The organic phase was concentrated under reduced pressure so as to obtain a crude product. The resulting crude product was used as-is in the following step.

(3) The crude product obtained in the item (2) and the following reagent and solvents were put into a reaction container.

tetrahydrofuran: 10 ml
methanol: 40 ml
paratoluenesulfonic acid: a small amount

Subsequently, the reaction solution was agitated at room temperature for 10 hours. At this time, the degree of proceeding of the reaction was ascertained with TLC appropriately. Then, generated precipitates were filtrated and recovered and were subjected to recrystallization with a chloroform/hexane mixed solvent, so that 4.1 g (yield 73%) of 4-(4-(2-hydroxyethylthio)phenyl)-4'-(2-hydroxyethyloxy)diphenyl sulfone was obtained.

(4) In Example 1 (3), 4-(4-(2-hydroxyethylthio)phenyl)-4'-(2-hydroxyethyloxy)diphenyl sulfone was used in place of 4,4'-bis(4-(2-hydroxyethoxy)phenyl)diphenyl sulfone. Synthesis was performed in a manner similar to that in Example 1 (3) except this, so as to obtain 2.5 g (yield 63%) of 4-(4-(2-methacryloyloxyethylthio)phenyl)-4'-(2-methacryloyloxyethyloxy)diphenyl sulfone. In the present example, the usage of methacrylic acid was 20 ml.

The structure of the resulting compound was ascertained with $^1$H-NMR.

$^1$H-NMR ($CDCl_3$; TMS): δ 1.92 (s, 3H), 1.95 (s, 3H), 3.22 (t, 2H), 4.25 (t, 2H), 4.27 (t, 2H), 4.50 (t, 2H), 5.57 (d, 1H), 5.58 (d, 1H), 6.12 (d, 1H), 6.12 (d, 1H), 6.94-7.03 (m, 4H), 7.47-7.67 (m, 4H), 7.89-7.99 (m, 4H)

Example 3

The synthesis scheme of a compound synthesized in Example 3 will be described below. Furthermore, a specific synthesis method will be explained below.

(1) The following reagents and solvents were put into a reaction container.

4,4'-dichlorodiphenyl sulfone: 10 g
4-hydroxyphenylboric acid: 5.8 g
sodium hydrogen carbonate: 10 g
dioxane: 400 ml
water: 200 ml
tetrakistriphenylphosphine palladium: 0.8 g Subsequently, the reaction solution was heated to 90° C. and agitation was performed at this temperature (90° C.) for 10 hours. At this time, the degree of proceeding of the reaction was ascertained with TLC appropriately. Then, the reaction was terminated with an ammonium chloride aqueous solution, and an organic phase was extracted with ethyl acetate. The resulting organic phase was washed with water and saturated saline solution in that order and was dried with anhydrous magnesium sulfate. A crude product obtained by concentrating the organic phase under reduced pressure was refined through column chromatography. The thus obtained product was used as-is in the following step.

(2) The following reagent and solvent were put into a reaction container.

sodium hydride: 1.4 g
N,N-dimethylformamide: 200 ml

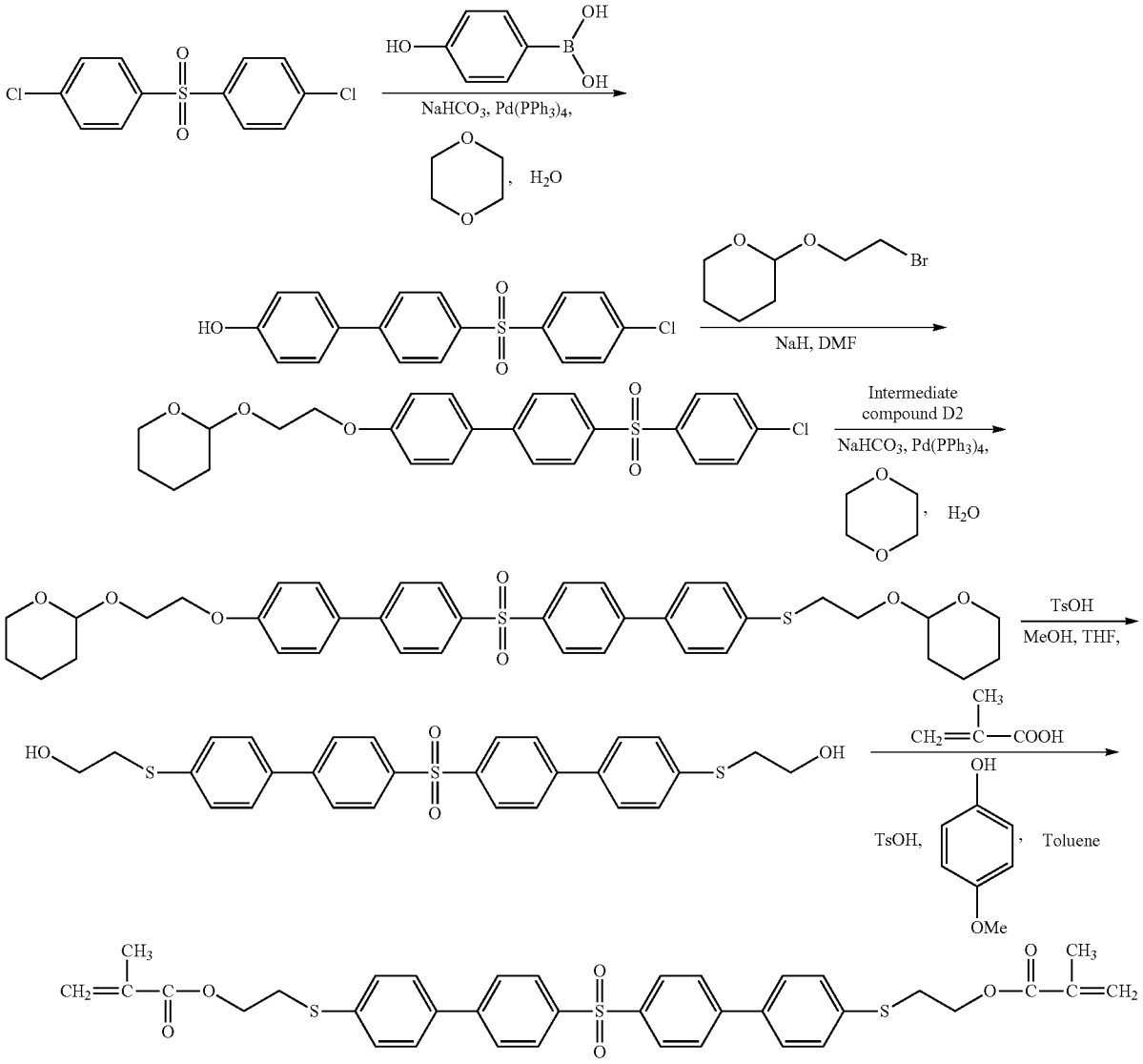

After the reaction solution was cooled to 0° C., the compound obtained in the item (1) was added gradually. Subsequently, the reaction solution was agitated for 2 hours while the temperature of the reaction solution was raised to room temperature. Then, 6.4 ml of 2-(2-bromoethoxy)tetrahydro-2H-pyran was added, the reaction solution was heated to 60° C., and agitation was performed at this temperature (60° C.) for 5 hours. At this time, the degree of proceeding of the reaction was ascertained with TLC appropriately. Thereafter, the reaction was terminated with an ammonium chloride aqueous solution, and an organic phase was extracted with ethyl acetate. The resulting organic phase was washed with water and saturated saline solution in that order and was dried with anhydrous magnesium sulfate. A crude product obtained by concentrating the organic phase under reduced pressure was refined through column chromatography. The thus obtained product was used as-is in the following step.

(3) The product obtained in the item (2) and the following reagents and solvents were put into a reaction container.

Intermediate compound D2: 6.6 g
sodium hydrogen carbonate: 4.5 g
dioxane: 300 ml
water: 150 ml
tetrakistriphenylphosphine palladium: 0.3 g Subsequently, the reaction solution was heated to 90° C. and agitation was performed at this temperature (90° C.) for 20 hours. At this time, the degree of proceeding of the reaction was ascertained with TLC appropriately. Then, the reaction was terminated with an ammonium chloride aqueous solution, and an organic phase was extracted with ethyl acetate. The resulting organic phase was washed with water and saturated saline solution in that order and was dried with anhydrous magnesium sulfate. A crude product obtained by concentrating the organic phase under reduced pressure was refined through column chromatography. The thus obtained product was used as-is in the following step.

(4) The product obtained in the item (3) and the following reagent and solvents were put into a reaction container.

tetrahydrofuran: 10 ml
methanol: 40 ml
paratoluenesulfonic acid: a small amount

Subsequently, the reaction solution was agitated at room temperature for 12 hours. The degree of proceeding of the reaction was ascertained with TLC appropriately. After generated precipitates were filtrated and recovered, the resulting precipitates were subjected to recrystallization with a chloroform/hexane mixed solvent, so that 5 g (yield 28%) of 4-(4-(2-hydroxyethylthio)phenyl)-4'-(4-(2-hydroxyethyloxy)phenyl)diphenyl sulfone was obtained.

(5) In Example 1 (3), 4-(4-(2-hydroxyethylthio)phenyl)-4'-(4-(2-hydroxyethyloxy)phenyl)diphenyl sulfone (2.0 g) was used in place of 4,4'-bis(4-(2-hydroxyethoxy)phenyl) diphenyl sulfone. Synthesis was performed in a manner similar to that in Example 1 (3) except this, so as to obtain 0.8 g (yield 31%) of 4-(4-(2-methacryloyloxyethylthio)phenyl)-4'-(4-(2-methacryloyloxyethyloxy)phenyl)diphenyl sulfone. In the present example, the usage of methacrylic acid was 20 ml.

The structure of the resulting compound was ascertained with $^1$H-NMR.

$^1$H-NMR ($CDCl_3$; TMS): δ 1.91 (s, 3H), 1.95 (s, 3H), 3.24 (t, 2H), 4.27 (t, 2H), 4.35 (t, 2H), 4.52 (t, 2H), 5.56-5.60 (m, 2H), 6.09-6.13 (m, 2H), 6.98-7.02 (m, 2H), 7.45-7.69 (m, 12H), 7.98-8.02 (m, 2H)

Example 4

The synthesis scheme of a compound synthesized in Example 4 will be described below. Furthermore, a specific synthesis method will be explained below.

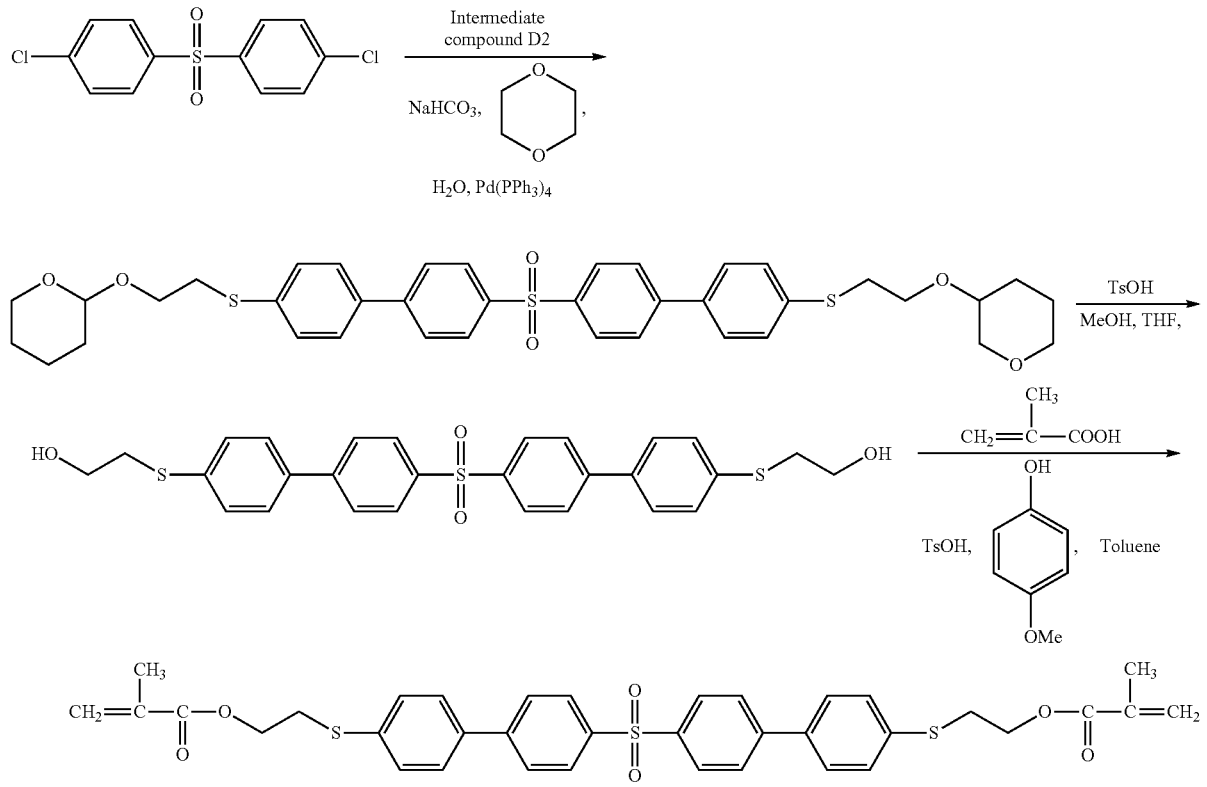

(1) The following reagents and solvents were put into a reaction container.

4,4'-dichlorodiphenyl sulfone: 13 g
Intermediate compound D2: 50 g
sodium hydrogen carbonate: 29 g
dioxane: 400 ml
water: 200 ml
tetrakistriphenylphosphine palladium: 2.1 g Subsequently, the reaction solution was heated to 90° C. and agitation was performed at this temperature (90° C.) for 20 hours. At this time, the degree of proceeding of the reaction was ascertained with TLC appropriately. Then, the reaction was terminated with an ammonium chloride aqueous solution, and an organic phase was extracted with ethyl acetate. The resulting organic phase was washed with water and saturated saline solution in that order and was dried with anhydrous magnesium sulfate. A crude product obtained by concentrating the organic phase under reduced pressure was refined through column chromatography. The thus obtained product was used as-is in the following step.

(2) The product obtained in the item (1) and the following reagent and solvents were put into a reaction container.

tetrahydrofuran: 30 ml
methanol: 100 ml
paratoluenesulfonic acid: a small amount Subsequently, the reaction solution was agitated at room temperature for 12 hours. At this time, the degree of proceeding of the reaction was ascertained with TLC appropriately. After generated precipitates were filtrated and recovered, recrystallization with a chloroform/hexane mixed solvent was performed, so that 19 g (yield 74%) of 4,4'-bis(4-(2-hydroxyethylthio)phenyl)diphenyl sulfone was obtained.

(3) In Example 1 (3), 4,4'-bis(4-(2-hydroxyethylthio)phenyl)diphenyl sulfone was used in place of 4,4'-bis(4-(2-hydroxyethoxy)phenyl)diphenyl sulfone. Synthesis was performed in a manner similar to that in Example 1 (3) except this, so as to obtain 3.0 g (yield 80%) of 4,4'-bis(4-(2-methacryloyloxyethylthio)phenyl)diphenyl sulfone. In the present example, the usages of methacrylic acid and toluene were 29 ml and 40 ml, respectively.

The structure of the resulting compound was ascertained with $^1$H-NMR.

$^1$H-NMR ($CDCl_3$; TMS): δ 1.91 (s, 6H), 3.22 (t, 4H), 4.35 (t, 4H), 5.56 (s, 2H), 6.07 (s, 2H), 7.42-7.52 (m, 8H), 7.65-7.71 (m, 4H), 8.00-8.05 (m, 4H)

Example 9

The synthesis scheme of a compound synthesized in Example 9 will be described below. Furthermore, a specific synthesis method will be explained below.

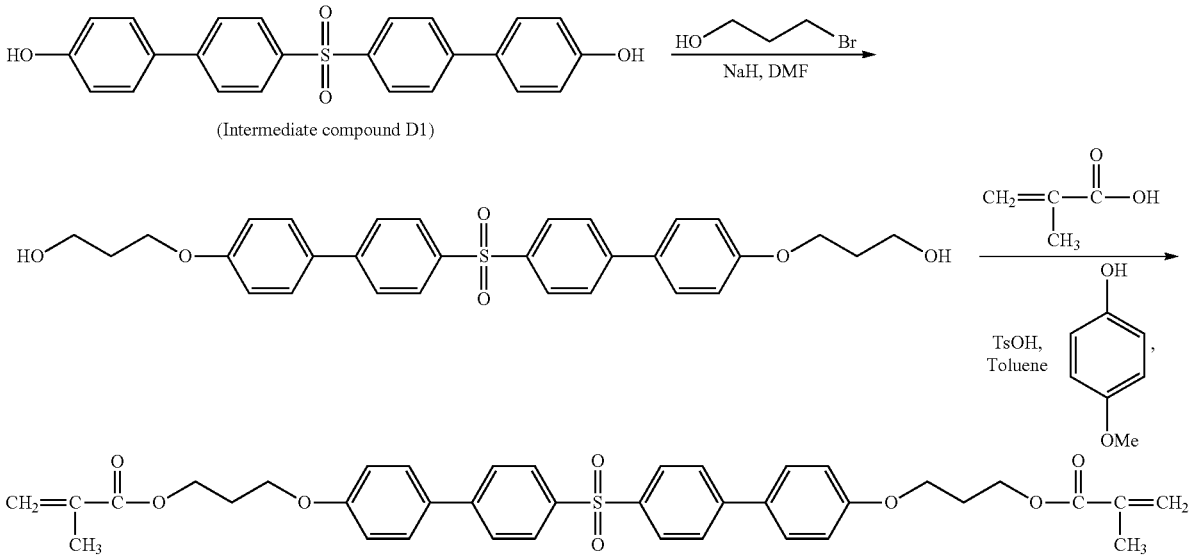

(1) The following reagent and solvent were put into a reaction container.

sodium hydride (55%): 2.5 g
N,N-dimethylformamide: 200 ml

After the reaction solution was cooled to 0° C., Intermediate compound D1 (10 g) was added gradually. Subsequently, the reaction solution was agitated while the temperature was raised to room temperature. Then, 5.4 ml of 3-bromopropanol was added, the reaction solution was heated to 50° C., and agitation was performed at this temperature (50° C.) for 12 hours. At this time, the degree of proceeding of the reaction was ascertained with TLC appropriately. Thereafter, the reaction was terminated with water, and an organic phase was extracted with ethyl acetate. The resulting organic phase was washed with water and saturated saline solution in that order and was dried with anhydrous magnesium sulfate. A crude product obtained by concentrating the organic phase under reduced pressure was subjected to recrystallization with a hexane/ethyl acetate mixed solution, so that a white crystal was obtained. The thus obtained white crystal was used as-is in the following step.

(2) In Example 5 (3), the white crystal obtained in the item (1) in the present example was used in place of 4,4'-bis(4-(2-hydroxyethoxy)phenyl)diphenyl sulfone. In a manner similar to that in Example 5 (3) except this, 11.5 g (yield 71%) of 4,4'-bis(4-(3-methacryloyloxypropoxy)phenyl)diphenyl sulfone was obtained. In the present example, the usages of methacrylic acid, paratoluenesulfonic acid, methoxyphenol, and toluene were 90 ml, 0.6 g, 0.6 g, and 90 ml, respectively.

The structure of the resulting compound was ascertained with $^1$H-NMR.

$^1$H-NMR ($CDCl_3$; TMS): δ 1.94 (s, 6H), 2.19 (dt, 4H), 4.11 (t, 4H), 4.36 (t, 4H), 5.56 (br, 2H), 6.11 (br, 2H), 6.94-6.99 (m, 4H), 7.45-7.54 (m, 4H), 7.63-7.69 (m, 4H), 7.96-8.03 (m, 4H)

Example 5

The synthesis scheme of a compound synthesized in Example 5 will be described below. Furthermore, a specific synthesis method will be explained below.

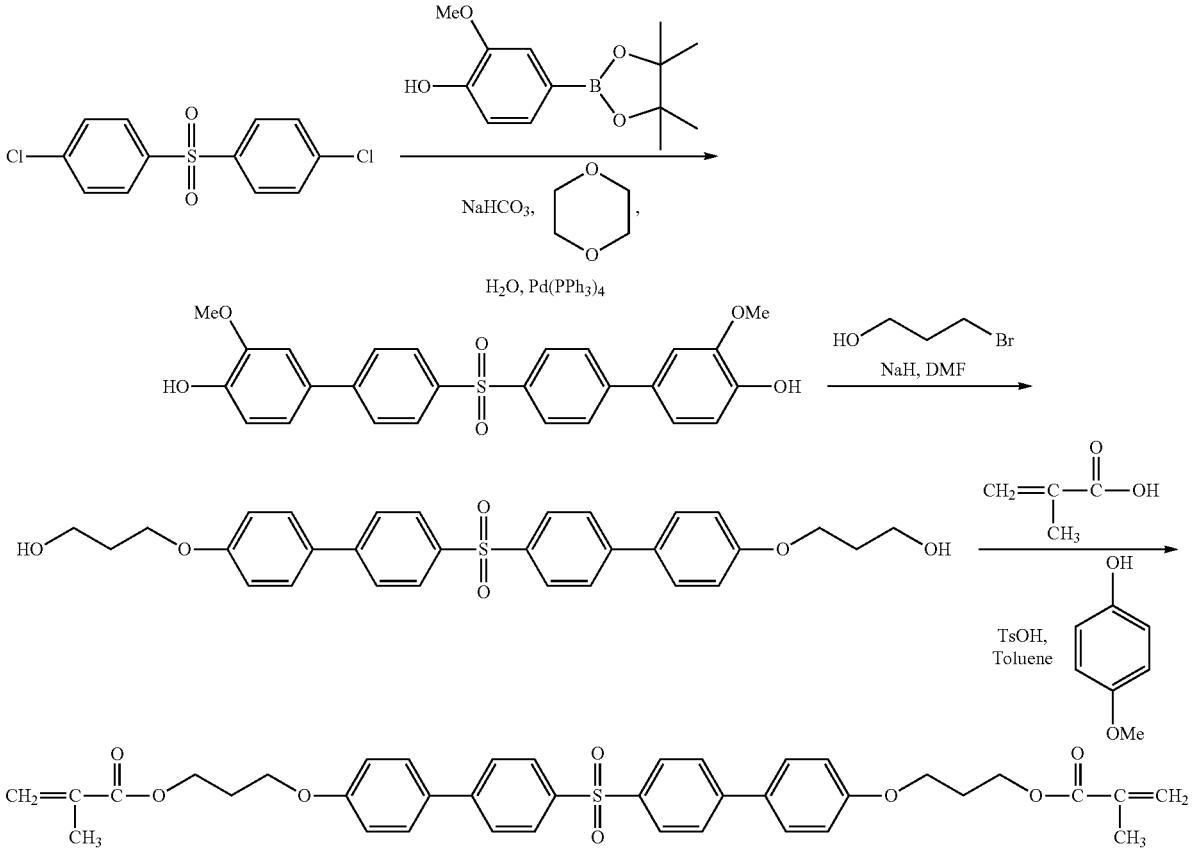

(1) The following reagents and solvents were put into a reaction container.

4,4'-dichlorodiphenyl sulfone: 10 g 2-methoxy-4-(4,4,5,5-tetramethyl-1,3,2-dioxabororan-2-yl) phenol: 25 g sodium hydrogen carbonate: 25 g 1,4-dioxane: 500 ml water: 250 ml tetrakistriphenylphosphine palladium: 2.5 g Subsequently, the reaction solution was heated to 90° C. and agitation was performed at this temperature (90° C.) for 20 hours. At this time, the degree of proceeding of the reaction was ascertained with TLC appropriately. Then, the reaction solution was diluted with water, and an organic phase was recovered through solvent extraction. The resulting organic phase was washed with water and saturated saline solution in that order. The organic phase was dried with anhydrous magnesium sulfate and was concentrated under reduced pressure, so as to produce a crude product. Thereafter, the resulting crude product was subjected to recrystallization with a hexane/ethyl acetate mixed solvent, so that 4,4'-bis(4-hydroxy-3-methoxyphenyl)diphenyl sulfone was obtained as a light yellow crystal. The thus obtained light yellow crystal was used as-is in the following step.

(2) The following reagent and solvent were put into a reaction container.

sodium hydride (55%): 5.1 g

N,N-dimethylformamide: 300 ml

The light yellow crystal obtained in the item (1) was added to the reaction solution gradually. Subsequently, the reaction solution was agitated at room temperature for 1 hour. Then, 10 ml of 3-bromopropanol was added gradually, the reaction solution was heated to 60° C., and agitation was performed at this temperature (60° C.) for 12 hours. At this time, the degree of proceeding of the reaction was ascertained with TLC appropriately. Thereafter, the reaction was terminated with water, and an organic phase was extracted with ethyl acetate. The resulting organic phase was washed with water and saturated saline solution in that order and was dried with anhydrous magnesium sulfate. A crude product obtained by concentrating the organic phase under reduced pressure was subjected to recrystallization with a hexane/ethyl acetate mixed solvent, so that a white crystal was obtained. The thus obtained white crystal was used as-is in the following step.

(3) In Example 1 (3), the white crystal obtained in the item (2) in the present example was used in place of 4,4'-bis(4-(2-hydroxyethoxy)phenyl)diphenyl sulfone. In a manner similar to that in Example 1 (3) except this, 21 g (yield 84%) of 4,4'-bis (4-(3-methacryloyloxypropoxy)-3-methoxyphenyl)diphenyl sulfone was obtained. In the present example, the usages of methacrylic acid, paratoluenesulfonic acid, methoxyphenol, and toluene were 120 ml, 1.3 g, 11.3 g, and 300 ml, respectively.

The structure of the resulting compound was ascertained with $^1$H-NMR.

$^1$H-NMR ($CDCl_3$; TMS): δ 1.94 (s, 6H), 2.24 (dt, 4H), 3.91 (s, 6H), 4.17 (t, 4H), 4.37 (t, 4H), 5.56 (br, 2H), 6.11 (br, 2H), 6.92-7.15 (m, 6H), 7.64-7.70 (m, 4H), 7.97-8.03 (m, 4H)

Example 6

The synthesis scheme of a compound synthesized in Example 6 will be described below. Furthermore, a specific synthesis method will be explained below.

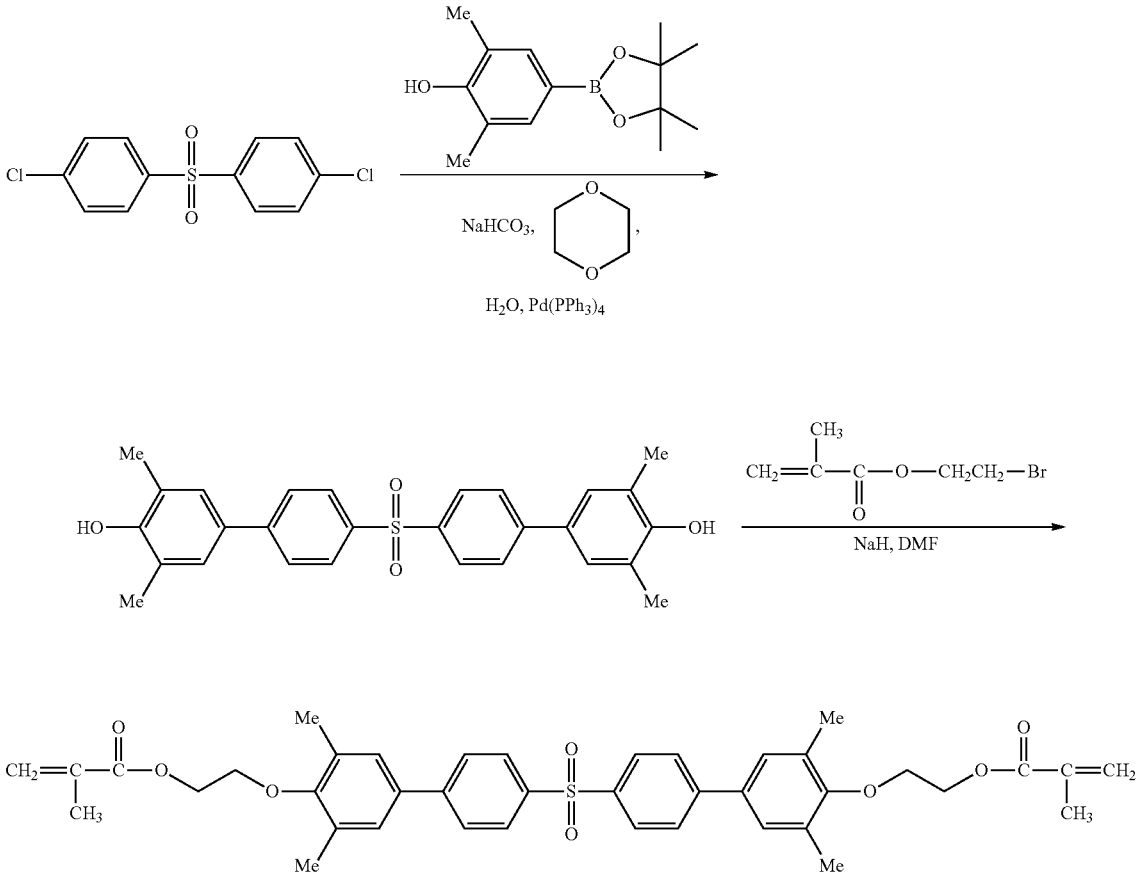

(1) Synthesis was performed in a manner similar to that in Example 10 (1) except that 2,6-dimethyl-4-(4,4,5,5-tetramethyl-1,3,2-dioxabororan-2-yl)phenol was used in place of 2-methoxy-4-(4,4,5,5-tetramethyl-1,3,2-dioxabororan-2-yl) phenol in Example 5 (1). In the present example, the usages of 4,4'-dichlorodiphenyl sulfone and tetrakistriphenylphosphine palladium were 9.6 g and 2.3 g, respectively. In this manner, 4,4'-bis(4-hydroxy-3,5-dimethylphenyl)diphenyl sulfone was obtained as a white crystal. The thus obtained white crystal was used as-is in the following step.

(2) The following reagent and solvent were put into a reaction container.

sodium hydride (55%): 3.1 g

N,N-dimethylformamide: 300 ml

The white crystal obtained in the item (1) was added to the reaction solution gradually. Subsequently, the reaction solution was agitated at room temperature for 1 hour. Then, 15 g of 2-bromoethyl methacrylate was added gradually, the reaction solution was heated to 60° C., and agitation was performed at this temperature (60° C.) for 12 hours. At this time, the degree of proceeding of the reaction was ascertained with TLC appropriately. Thereafter, the reaction was terminated by adding water, and an organic phase was extracted with ethyl acetate. The resulting organic phase was washed with water and saturated saline solution in that order and was dried with anhydrous magnesium sulfate. A crude product obtained by concentrating the organic phase under reduced pressure was refined through column chromatography, so that 15 g (yield 66%) of 4,4'-bis(4-(2-methacryloyloxyethoxy)-3,5-dimethylphenyl)diphenyl sulfone.

The structure of the resulting compound was ascertained with $^1$H-NMR.

$^1$H-NMR ($CDCl_3$; TMS): δ 1.89 (s, 6H), 2.30 (s, 12H), 4.30 (t, 4H), 4.62 (s, 4H), 5.47 (br, 2H), 6.05 (br, 2H), 7.21-7.27 (m, 4H), 7.60-7.67 (m, 4H), 7.93-8.01 (m, 4H)

Example 8

The synthesis scheme of a compound synthesized in Example 8 will be described below. Furthermore, a specific synthesis method will be explained below.

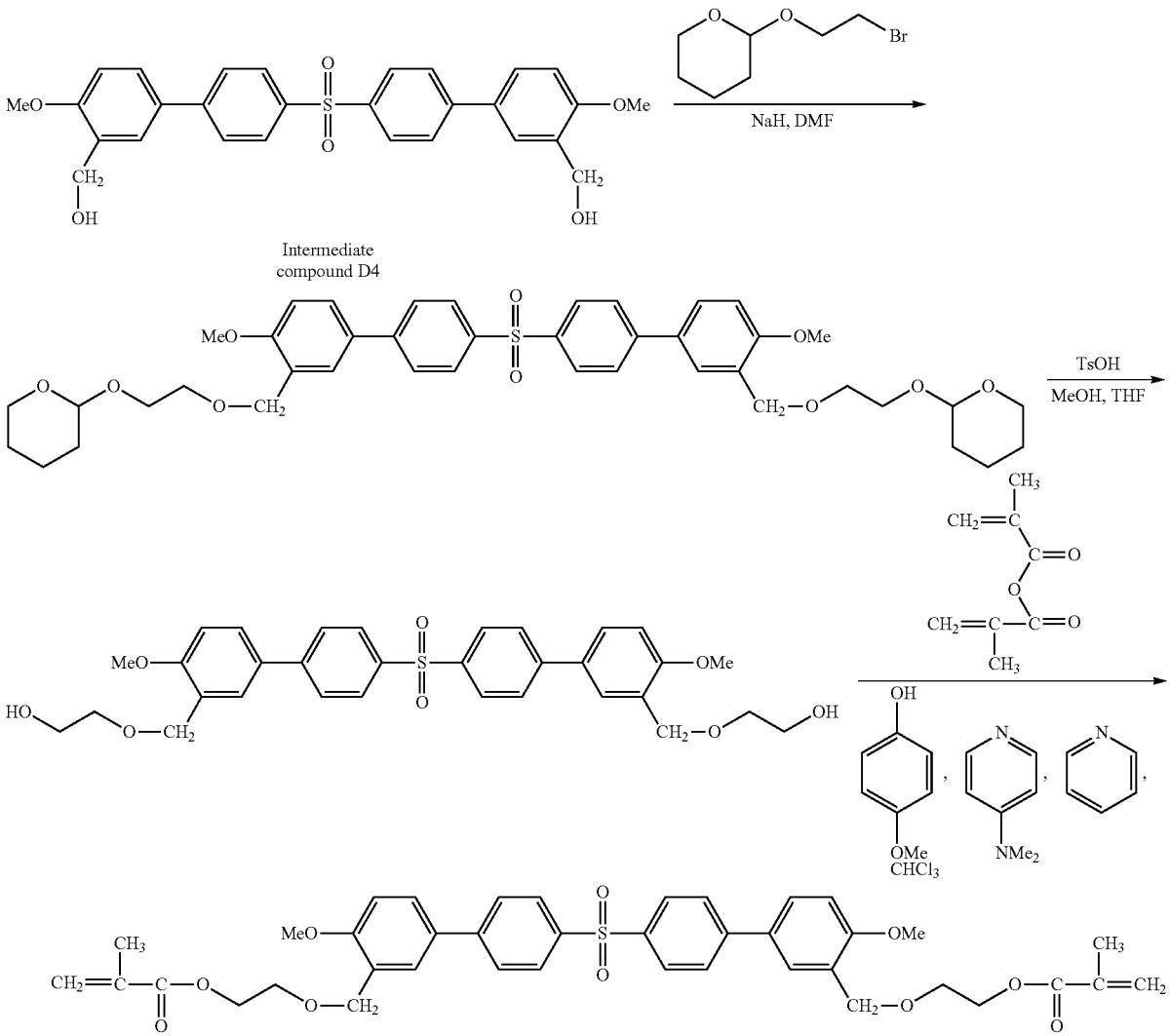

(1) The following reagent and solvent were put into a reaction container.

sodium hydride (55%): 11 g

N,N-dimethylformamide: 300 ml solution

After the reaction solution was cooled to 0° C., Intermediate compound D4 (30 g) was added gradually. Subsequently, the reaction solution was agitated at the same temperature (0° C.) for 1 hour. Then, 36 ml of 2-(2-bromoethoxy)tetrahydro-2H-pyran was added, the reaction solution was heated to 70° C., and agitation was performed at this temperature (70° C.) for 6 hours. At this time, the degree of proceeding of the reaction was ascertained with TLC appropriately. Thereafter, the reaction was terminated by adding water, and an organic phase was extracted with ethyl acetate. The resulting organic phase was washed with water and saturated saline solution in that order and was dried with anhydrous magnesium sulfate. A crude product obtained by concentrating the organic phase under reduced pressure was refined through column chromatography, so that a light yellow liquid was obtained. The thus obtained light yellow liquid was used as-is in the following step.

(2) The light yellow liquid obtained in the item (1) and the following reagent and solvents were put into a reaction container.

methanol: 150 ml tetrahydrofuran: 50 ml paratoluenesulfonic acid: an amount of catalyst Subsequently, the reaction solution was agitated at room temperature for 12 hours. At this time, the degree of proceeding of the reaction was ascertained with TLC appropriately. After the reaction was terminated by adding triethylamine, the generated crystal was filtrated and recovered. The resulting crystal was subjected to recrystallization with a hexane/ethyl acetate mixed solvent, so that a white crystal was obtained. The thus obtained white solid was used as-is in the following step.

(3) The white solid obtained in the item (2) and the following reagents and solvents were put into a reaction container.

chloroform: 100 ml pyridine: 150 ml 4-methoxyphenol: 0.2 g

N,N-dimethylaminopyridine: 1.2 g (meth)acrylic acid anhydride: 30 ml

Subsequently, the reaction solution was agitated at room temperature for 12 hours. At this time, the degree of proceeding of the reaction was ascertained with TLC appropriately. Thereafter, the reaction was terminated by adding 2 N hydrochloric acid, and an organic phase was extracted with toluene. The resulting organic phase was washed with 2 N hydrochloric acid, 10% sodium hydroxide aqueous solution, water, and saturated saline solution in that order and was dried with anhydrous magnesium sulfate. A crude product obtained by concentrating the organic phase under reduced pressure was refined through column chromatography, so that an oily product was obtained. The resulting oily product was subjected to recrystallization with a hexane/ethyl acetate mixed solvent, so as to obtain 26 g (yield 55%) of 4,4'-bis((3-(2-methacryloyloxyethoxy)methyl)-4-methoxyphenyl)diphenyl sulfone.

The structure of the resulting compound was ascertained with $^1$H-NMR.

$^1$H-NMR ($CDCl_3$; TMS): δ 1.89 (s, 6H), 3.78 (t, 4H), 3.87 (s, 6H), 4.35 (t, 4H), 4.65 (s, 4H), 5.49 (br, 2H), 6.09 (br, 2H), 6.90-6.98 (m, 2H), 7.45-7.51 (m, 2H), 7.60-7.72 (m, 8H), 7.94-8.02 (m, 4H)

(3) In Example 8 (3), the white solid obtained in the present example (2) was used in place of the white solid obtained in Example 8 (2). In a manner similar to that in Example 8 (2), 6.7 g (yield 53%) of compound described below, that is, 4,4'-bis ((3 -(4-methacryloyloxybutoxy) methyl)-4-methoxyphenyl)diphenyl sulfone was obtained.

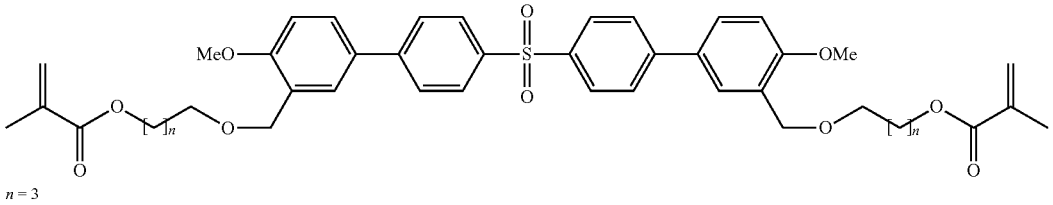

The structure of the resulting compound was ascertained with $^1$H-NMR.

$^1$H-NMR ($CDCl_3$; TMS): δ 1.89 (s, 6H), 2.24 (dt, 4H), 3.73 (t, 4H), 3.85 (s, 6H), 4.32 (t, 4H), 4.65 (s, 4H), 5.49 (br, 2H), 6.09 (br, 2H), 6.91-6.99 (m, 2H), 7.45-7.52 (m, 2H), 7.59-7.72 (m, 8H), 7.93-8.02 (m, 4H)

Comparative Example 1

The compound described below was synthesized and experiments on the optical characteristics and the practicality described later were performed. A synthesis method of the compound in the present comparative example will be explained below.

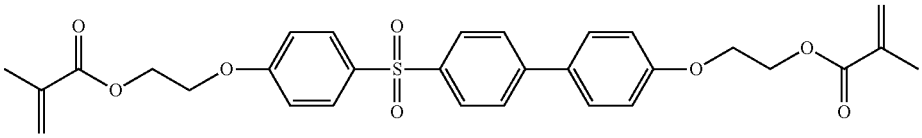

Example 9

A specific synthesis method of a compound synthesized in Example 9 will be explained below.

(1) In Example 12 (1), 2-(4-chlorobutoxy)tetrahydro-2H-pyran (9.0 ml) described below was used in place of 2-(2-bromoethoxy)tetrahydro-2H-pyran. Synthesis was performed in a manner similar to that in Example 8 (1) except this and, thereby, a light yellow liquid product was obtained. In the present example, the usages of sodium hydride (55%) and Intermediate compound D4 were 2.8 g and 8.0 g, respectively. The thus obtained light yellow liquid was used as-is in the following step.

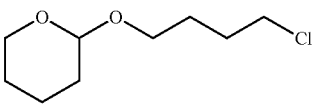

(2) A white crystal was obtained in a manner similar to the method in Example 8 (2) except that in Example 8 (2), the light yellow liquid obtained in the present example (1) was used in place of the light yellow liquid obtained in Example 8 (1). The thus obtained white solid was used as-is in the following step.

(1) The following reagents and solvents were put into a reaction container.

Intermediate compound D3: 5 g
4-hydroxyphenylboric acid: 2.5 g
sodium hydrogen carbonate: 4 g
dioxane: 200 ml
water: 100 ml
tetrakistriphenylphosphine palladium: 0.3 g Subsequently, the reaction solution was heated to 90° C. and agitation was performed at this temperature (90° C.) for hours. At this time, the degree of proceeding of the reaction was ascertained with TLC appropriately. Then, the reaction was terminated by adding an ammonium chloride aqueous solution, and an organic phase was extracted with ethyl acetate. The resulting organic phase was washed with water and saturated saline solution in that order and was dried with anhydrous magnesium sulfate. A crude product obtained by concentrating the organic phase under reduced pressure was refined through column chromatography, so that 4.2 g (yield 98%) of 4-(4-hydroxyphenyl)-4'-hydroxydiphenyl sulfone was obtained.

(2) The following reagent and solvent were put into a reaction container.

sodium hydride: 1.2 g
N,N-dimethylformamide: 150 ml

After the reaction solution was cooled to 0° C., 4.2 g of 4-(4-hydroxyphenyl)-4'-hydroxydiphenyl sulfone obtained in the item (1) was added at the same temperature (0° C.) gradually. Subsequently, the reaction solution was agitated for 2 hours while the temperature was raised to room temperature. Then, 4.8 ml of 2-(2-bromoethoxy)tetrahydro-2H-pyran was added, the reaction solution was heated to 60° C., and agitation was performed at this temperature (60° C.) for 12 hours. At this time, the degree of proceeding of the reaction was ascertained with TLC. Thereafter, the reaction was terminated by adding an ammonium chloride aqueous solution, and an organic phase was extracted with ethyl acetate. The resulting organic phase was washed with water and saturated saline solution in that order and was dried with anhydrous magnesium sulfate. A crude product obtained by concentrating the organic phase under reduced pressure was refined through column chromatography. The thus obtained product was used as-is in the following step.

(3) The product obtained in the item (2) and the following reagent and solvents were put into a reaction container.

tetrahydrofuran: 10 ml
methanol: 40 ml
paratoluenesulfonic acid: a small amount

Subsequently, the reaction solution was agitated at room temperature for 12 hours. At this time, the degree of proceeding of the reaction was ascertained with TLC appropriately. After generated precipitates were filtrated and recovered, recrystallization with a chloroform/hexane mixed solvent was performed, so that 5.0 g (yield 92%) of 4-(4-(2-hydroxyethyloxy)phenyl)-4'-(2-hydroxyethyloxy)diphenyl sulfone was obtained.

(4) The following reagents and solvent were put into a reaction container.

4-(4-(2-hydroxyethyloxy)phenyl)-4'-(2-hydroxyethyloxy) diphenyl sulfone: 4.0 g
methacrylic acid: 25 ml
paratoluenesulfonic acid: 0.2 g
4-methoxyphenol: 0.2 g
toluene: 30 ml Then, the reaction solution was heated and agitated for 20 hours. At this time, generated water was removed appropriately, and the degree of proceeding of the reaction was ascertained with TLC appropriately. The reaction solution was neutralized by adding a sodium hydroxide aqueous solution, and an organic phase was extracted with chloroform. The resulting organic phase was washed with water and saturated saline solution in that order and was dried with anhydrous magnesium sulfate. Next, a crude product obtained by concentrating the organic phase under reduced pressure was refined through column chromatography, so that 4.3 g (yield 81%) of 4-(4-(2-methacryloyloxyethyloxy) phenyl)-4'-(2-methacryloyloxyethyloxy)diphenyl sulfone was obtained.

The structure of the resulting compound was ascertained with $^1$H-NMR.

$^1$H-NMR ($CDCl_3$; TMS): δ 1.92 (s, 3H), 1.95 (s, 3H), 4.20-4.29 (m, 4H), 4.46-4.52 (m, 4H), 5.58 (d, 1H), 5.58 (d, 1H), 6.12 (d, 1H), 6.12 (d, 1H), 6.94-7.03 (m, 4H), 7.47-7.54 (m, 2H), 7.61-7.67 (m, 2H), 7.88-7.97 (m, 4H)

Comparative Example 2

Synthesis of 4,4'-bis(2-methylthiophenyl)diphenyl sulfone

The compound (4,4'-bis(2-methylthiophenyl)diphenyl sulfone) described below was synthesized and experiments on the optical characteristics and the practicality described later were performed. A synthesis method of the compound in the present comparative example will be explained below.

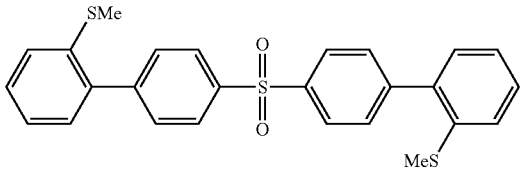

(1) The following reagents and solvents were put into a reaction container.

4,4'-dichlorodiphenyl sulfone: 0.4 g
2-methylthiophenylboric acid: 0.6 g
sodium hydrogen carbonate: 0.8 g
1,4-dioxane: 20 ml
water: 10 ml
tetrakistriphenylphosphine palladium: 0.07 g Subsequently, the reaction solution was heated to 90° C. and agitation was performed at this temperature for 20 hours. At this time, the degree of proceeding of the reaction was ascertained with TLC appropriately. Then, the reaction solution was diluted with water, and an organic phase was recovered through solvent extraction. The resulting organic phase was washed with water and saturated saline solution in that order. The resulting organic phase was dried with anhydrous magnesium sulfate and, thereafter, a crude product was obtained through concentration under reduced pressure. The resulting crude product was subjected to recrystallization with a hexane/ethyl acetate mixed solvent, so that 0.5 g (yield 72%) of 4,4'-bis(2-methylthiophenyl)diphenyl sulfone was obtained as a light yellow crystal.

The structure of the resulting compound was ascertained with $^1$H-NMR.

$^1$H-NMR ($CDCl_3$; TMS): δ 2.37 (s, 6H), 7.14-7.40 (m, 8H), 7.56-7.62 (m, 4H), 8.00-8.06 (m, 4H)

Comparative Example 3

Synthesis of 4-(4-methylthiophenyl)diphenyl ether

The compound (4-(4-methylthiophenyl)diphenyl ether) described below was synthesized and experiments on the optical characteristics and the practicality described later were performed. A synthesis method of the compound in the present comparative example will be explained below.

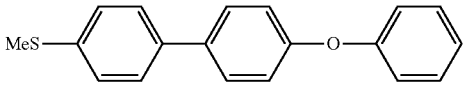

(1) The following reagents and solvents were put into a reaction container.

4-bromodiphenyl ether: 0.8 g
4-methylthiophenylboric acid: 0.6 g
sodium hydrogen carbonate: 0.8 g
dioxane: 20 ml
water: 10 ml
tetrakistriphenylphosphine palladium: 0.1 g Subsequently, the reaction solution was heated to 90° C. and agitation was performed at this temperature for 20 hours. At this time, the degree of proceeding of the reaction was ascertained with TLC appropriately. Then, the reaction solution was diluted with water, and an organic phase was recovered through solvent extraction. The resulting organic phase was washed with water and saturated saline solution in that order. The resulting organic phase was dried with anhydrous magnesium sulfate and, thereafter, a crude product was obtained through concentration under reduced pressure. The resulting crude product was subjected to recrystallization with a hexane/ethyl acetate mixed solvent, so that 0.8 g (yield 89%) of 4-(4-methylthiophenyl)diphenyl ether was obtained.

The structure of the resulting compound was ascertained with $^1$H-NMR.

$^1$H-NMR ($CDCl_3$; TMS): δ 2.51 (s, 3H), 7.03-7.15 (m, 4H), 7.28-7.39 (m, 5H), 7.46-7.55 (m, 4H)

Evaluation of Optical Characteristics

Regarding compounds synthesized in Examples and Comparative examples, evaluation of optical characteristics was performed by the following methods.

(1) Preparation of Evaluation Sample

Evaluation samples were produced by methods described below.

(1a) Sample for Measuring Refractive Index

Two disk-shaped glass substrates having a diameter of 20 mm were prepared. A compound to be measured was placed on a first glass substrate in such a way that the thickness became 12.5 μm uniformly. A second glass substrate was placed on the compound to be measured and, thereafter, the outer-areas of the glass substrates were sealed. In the case where the compound to be measured was a (meth)acrylate compound, the compound sandwiched between the two glass substrates was cured by applying ultraviolet rays to the sample. Meanwhile, in the case where the compound to be measured was a compound other than the (meth)acrylate compound, the compound sandwiched between the two glass substrates was melted by heating the sample.

(1b) Sample for Measuring Transmittance

A sample was produced in a manner similar to the method in the above-described item (1a) except that a thickness of the compound to be measured and placed on the first glass substrate was specified to be 50 μm or 500 μm in the above-described item (1a).

(2) Measurement and Evaluation

The refractive index was measured by using an Abbe refractometer (Kalnew Co., Ltd.). Regarding the transmittance, each of two types of films (50 μm, 500 μm) having different optical path lengths was formed, and measurement was performed by using a spectrophotometer U-4000 (product name) produced by Hitachi High-Technologies Corporation. The results in terms of internal transmittance (500 μm) at 410 nm are shown in Table 1. Here, the overall evaluation of the sample having optical characteristics within the range B shown in FIG. 1 and a transmittance at 410 nm of 90% or more is indicated by a symbol ○, and the overall evaluation of the other samples are indicated by a symbol x. The results thereof are shown in Table 1.

Evaluation of Stability

Regarding the stability, the sample exhibited no alteration after preservation in the air at 25° C. for 2 weeks was indicated by a symbol ○, and the sample exhibited alteration is indicated by a symbol x. In this regard, the sample having a polymerizable substituent was evaluated in the state of containing a small amount (1,000 ppm or less) of polymerization inhibitor. The results thereof are shown in Table 1.

TABLE 1

| | $n_d$ | $\nu_d$ | θg, F | Transmittance | Stability | Overall evaluation |
|---|---|---|---|---|---|---|
| Example 1 | 1.64 | 18.9 | 0.71 | 98 | ○ | ○ |
| Example 2 | 1.62 | 21.5 | 0.71 | 95 | ○ | ○ |
| Example 3 | 1.65 | 18.1 | 0.74 | 94 | ○ | ○ |
| Example 4 | 1.67 | 16.7 | 0.76 | 91 | ○ | ○ |
| Example 5 | 1.62 | 19.3 | 0.71 | 98 | ○ | ○ |
| Example 6 | 1.63 | 18.7 | 0.73 | 96 | ○ | ○ |
| Example 7 | 1.60 | 20.9 | 0.70 | 98 | ○ | ○ |
| Example 8 | 1.62 | 19.5 | 0.72 | 98 | ○ | ○ |
| Example 9 | 1.61 | 20.5 | 0.71 | 98 | ○ | ○ |
| Comparative example 1 | 1.61 | 23.3 | 0.68 | 97 | ○ | x |
| Comparative example 2 | 1.69 | 19.8 | 0.67 | 95 | ○ | x |
| Comparative example 3 | 1.78 | 20.2 | 0.69 | 98 | ○ | x |

The optical material organic compound and the optical material according to the present invention have characteristics that the dispersion characteristic (Abbe number ($\nu_d$)) and the secondary dispersion characteristic (θg,F) of the refractive index are high (high θg,F characteristic) and the chromatic aberration correction function delivers high performance. Consequently, it is possible to use for an apparatus, e.g., camera lenses, having a plurality of lenses.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-118823 filed May 24, 2010 and No. 2011-026381 filed Feb. 9, 2011, which are hereby incorporated by reference herein in their entirety.

What is claimed is:

1. [An optical material organic] *A* compound represented by the following general formula (1):

(1)

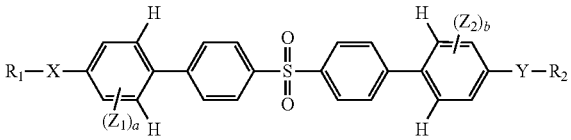

in the formula (1),

X and Y represent individually a substituent selected from the following substituents,

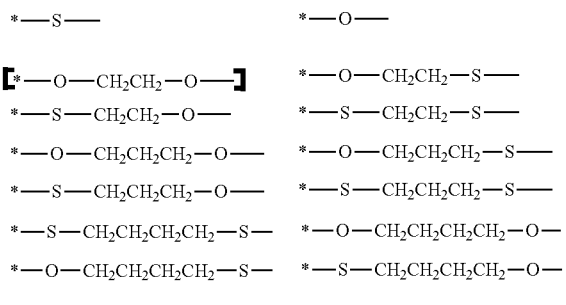

where a symbol * represents an end bonded to $R_1$ or $R_2$, $R_1$ and $R_2$ represent individually a substituent selected from the group consisting of [a hydrogen atom,] an alkyl group having the carbon number of 1 or 2, and a (meth)acryloyl group, $Z_1$ and $Z_2$ represent individually a substituent selected from the group consisting of a hydrogen atom, a halogen atom, an alkoxy group having the carbon number of 1 or 2, an alkylthio group having the carbon number of 1 or 2, *a methyl group, an ethyl group* and [a substituted or unsubstituted alkyl group having the carbon number of 1 or 2,] *a methyl or ethyl group having a substituent selected from the group consisting of a (meth)acryloyloxy group, a (meth)acryloyloxyethoxy group, a 2-hydroxyethoxy group, a 2-mercaptoethoxy group, a 2-mercaptoethylthio group, a (meth)acryloyloxypropoxy group, a 3-hydroxypropoxy group, a 3-mercaptopropoxy group, a 3-mercaptopropylthio group, a (meth)acryloyloxybutoxy group, a 4-hydroxybutoxy group, a 4-mercaptobutoxy group, a 4-mercaptobutylthio group, an allyloxy group, an allylthio group, a 4-vinylbenzyloxy group, an oxiranyl methoxy group, an oxiranyl ethoxy group, a thiiranyl methoxy group, a thiiranyl ethoxy group, a methylthio group, an ethylthio group, a methoxy group, and an ethoxy group, or a substituent represented by the following general formula (2):*

(2)

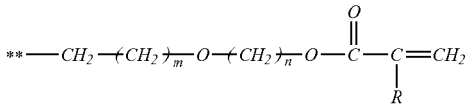

*where a symbol ** represents a bond, m represents 0 or 1, n represents an integer of 2 to 4 and R represents hydrogen or a methyl group,* a and b represent individually an integer of 0 to 2, two $Z_1$s may be the same or different when a is 2, and two $Z_2$s may be the same or different when b is 2.

2. The [optical material organic] compound according to claim 1, wherein X and Y represent individually a substituent selected from the following substituents:

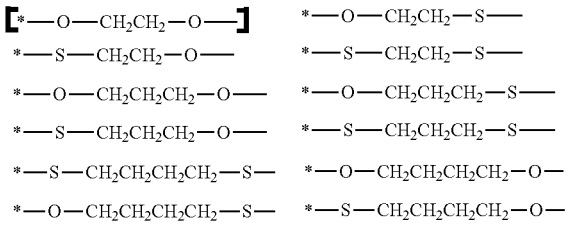

where a symbol * represents an end bonded to $R_1$ or $R_2$.

3. The [optical material organic] compound according to claim 1, wherein X and Y represent individually a substituent selected from the following substituents:

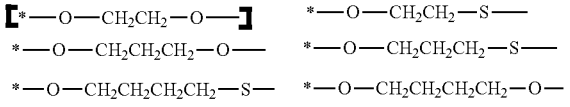

where a symbol * represents an end bonded to $R_1$ or $R_2$.

4. The [optical material organic] compound according to claim 1, wherein $R_1$ and $R_2$ represent individually [hydrogen or] a (meth)acryloyl group, X and Y represent individually a substituent selected from the following substituents:

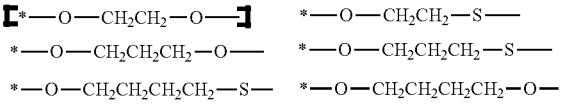

where a symbol * represents an end bonded to $R_1$ or $R_2$, and $Z_1$ and $Z_2$ represent individually a substituent selected from the group consisting of a hydrogen atom, a halogen atom, an alkoxy group having the carbon number of 1 or 2, an alkylthio group having the carbon number of 1 or 2, and an alkyl group having the carbon number of 1 or 2.

5. The [optical material organic] compound according to claim 1, wherein X and Y represent individually —S— or —O—, $R_1$ and $R_2$ represent individually [hydrogen or] an alkyl group having the carbon number of 1 or 2, and $Z_1$ and $Z_2$ represent individually a substituent selected from the group consisting of a hydrogen atom, a halogen atom, an alkoxy group having the carbon number of 1 or 2, an alkylthio group having the carbon number of 1 or 2, *a methyl group, an ethyl group* and [a substituted or unsubstituted alkyl group having the carbon number of 1 or 2] *a methyl or ethyl group having a substituent selected from the group consisting of a (meth)acryloyloxy group, a (meth)acryloyloxyethoxy group, a 2-hydroxyethoxy group, a 2-mercaptoethoxy group, a 2-mercaptoethylthio group, a (meth)acryloyloxypropoxy group, a 3-hydroxypropoxy group, a 3-mercaptopropoxy group, a 3-mercaptopropylthio group, a (meth)acryloyloxybutoxy group, a 4-hydroxybutoxy group, a 4-mercaptobutoxy group, a 4-mercaptobutylthio group, an allyloxy group, an allylthio group, a 4-vinylbenzyloxy group, an oxiranyl methoxy group, an oxiranyl ethoxy group, a thiiranyl methoxy group, a thiiranyl ethoxy group, a methylthio group, an ethylthio group, a methoxy group, and an ethoxy group, or a substituent represented by the following general formula (2):*

(2)

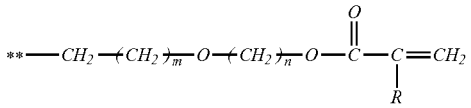

*where a symbol ** represents a bond, m represents 0 or 1, and n represents an integer of 2 to 4 and R represents hydrogen or a methyl group.*

6. The [optical material organic] compound according to claim 1, wherein X and Y represent individually —S— or —O—, $R_1$ and $R_2$ represent individually [hydrogen or] an alkyl group having the carbon number of 1 or 2, and $Z_1$ and $Z_2$ represent individually a hydrogen atom or [a substituted or unsubstituted alkyl group having the carbon number of 1 or 2] *a methyl or ethyl group having a substituent selected from the group consisting of a methyl group, an ethyl group, a (meth)acryloyloxy*

*group, a (meth)acryloyloxyethoxy group, a 2-hydroxyethoxy group, a 2-mercaptoethoxy group, a 2-mercaptoethylthio group, a (meth)acryloyloxypropoxy group, a 3-hydroxypropoxy group, a 3-mercaptopropoxy group, a 3-mercaptopropylthio group, a (meth)acryloyloxybutoxy group, a 4-hydroxybutoxy group, a 4-mercaptobutoxy group, a 4-mercaptobutylthio group, an allyloxy group, an allylthio group, a 4-vinylbenzyloxy group, an oxiranyl methoxy group, an oxiranyl ethoxy group, a thiiranyl methoxy group, a thiiranyl ethoxy group, a methylthio group, an ethylthio group, a methoxy group, and an ethoxy group, or a substituent represented by the following general formula (2):*

(2)

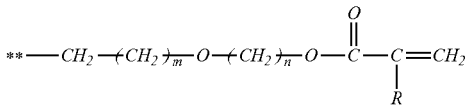

*where a symbol ** represents a bond, m represents 0 or 1, n represents an integer of 2 to 4 and R represents hydrogen or a methyl group.*

7. The [optical material organic] compound according to claim 1, wherein X and Y represent individually —S— or —O—, $R_1$ and $R_2$ represent individually an alkyl group having the carbon number of 1 or 2, and $Z_1$ and $Z_2$ represent individually a hydrogen atom, *a methyl group, an ethyl group,* or [a substituted or unsubstituted alkyl group having the carbon number of 1 or 2] *a methyl or ethyl group having a substituent selected from the group consisting of a (meth)acryloyloxy group, a (meth)acryloyloxyethoxy group, a 2-hydroxyethoxy group, a 2-mercaptoethoxy group, a 2-mercaptoethylthio group, a (meth)acryloyloxypropoxy group, a 3-hydroxypropoxy group, a 3-mercaptopropoxy group, a 3-mercaptopropylthio group, a (meth)acryloyloxybutoxy group, a 4-hydroxybutoxy group, a 4-mercaptobutoxy group, a 4-mercaptobutylthio group, an allyloxy group, an allylthio group, a 4-vinylbenzyloxy group, an oxiranyl methoxy group, an oxiranyl ethoxy group, a thiiranyl methoxy group, a thiiranyl ethoxy group, a methylthio group, an ethylthio group, a methoxy group, and an ethoxy group, or a substituent represented by the following general formula (2):*

(2)

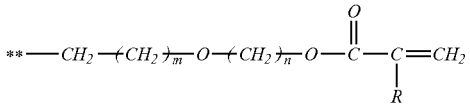

*where a symbol ** represents a bond, m represents 0 or 1, and n represents an integer of 2 to 4 and R represents hydrogen or a methyl group.*

8. The [optical material organic] compound according to claim 1, wherein $Z_1$ and/or $Z_2$ [represents an alkyl group which has the carbon number of 1 or 2 and which may have a substituent and the substituent is represented] *is represented* by the following general formula (2):

(2)

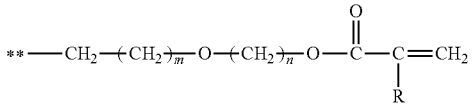

in the formula (2), a symbol ** represents a bond, m represents 0 or 1, n represents an integer of 2 to 4, and R represents hydrogen or a methyl group.

9. The [optical material organic] compound according to claim 8, wherein m is 0.

10. [An optical] *A* material comprising the [optical material organic] compound according to claim [8] *1*.

11. An optical element produced by molding the [optical] material according to claim [9] *10*.

12. [An optical material organic] *A* compound represented by the following general formula (3):

(3)

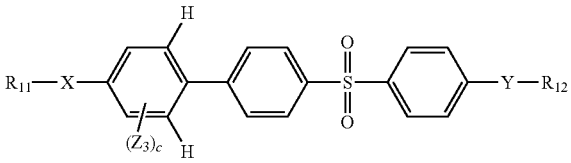

in the formula (3), X represents a substituent selected from the following substituents,

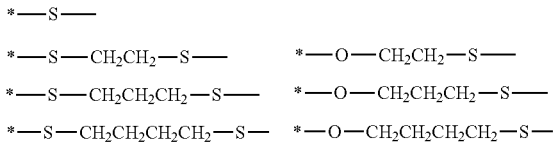

where a symbol * represents an end bonded to $R_{11}$,

Y represents a substituent selected from the following substituents,

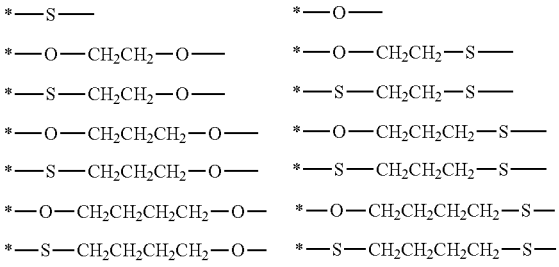

where a symbol * represents an end bonded to $R_{12}$, $R_{11}$ and $R_{12}$ represent individually a substituent selected from the group consisting of a hydrogen atom, an alkyl group having the carbon number of 1 or 2, and a (meth)acryloyl group, $Z_3$ represents a substituent selected from the group consisting of a hydrogen atom, a halogen atom, an alkoxy group having the carbon number of 1 or 2, an alkylthio group having the carbon number of 1 or 2, *a methyl*

*group, an ethyl group,* and [a substituted or unsubstituted alkyl group having the carbon number of 1 or 2] *a methyl or ethyl group having a substituent selected from the group consisting of a (meth)acryloyloxy group, a (meth)acryloyloxyethoxy group, a 2-hydroxyethoxy group, a 2-mercaptoethoxy group, a 2-mercaptoethylthio group, a (meth)acryloyloxypropoxy group, a 3-hydroxypropoxy group, a 3-mercaptopropoxy group, a 3-mercaptopropylthio group, a (meth)acryloyloxybutoxy group, a 4-hydroxybutoxy group, a 4-mercaptobutoxy group, a 4-mercaptobutylthio group, an allyloxy group, an allylthio group, a 4-vinylbenzyloxy group, an oxiranyl methoxy group, an oxiranyl ethoxy group, a thiiranyl methoxy group, a thiiranyl ethoxy group, a methylthio group, an ethylthio group, a methoxy group, and an ethoxy group, or a substituent represented by the following general formula (2):*

(2)

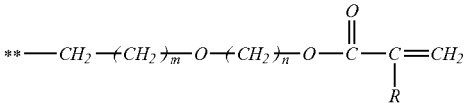

*where a symbol ** represents a bond, m represents 0 or 1, n represents an integer of 2 to 4 and R represents hydrogen or a methyl group,* c represents an integer of 0 to 2, and two $Z_3$s may be the same or different when c is 2.

13. The [optical material organic] compound according to claim 12, wherein X represents a substituent selected from the following substituents:

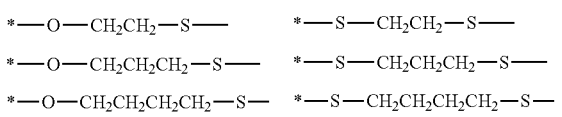

where a symbol * represents an end bonded to $R_{11}$, and

Y represents a substituent selected from the following substituents,

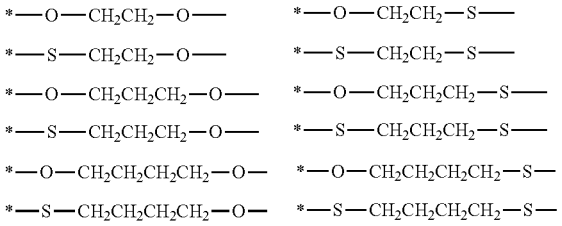

where a symbol * represents an end bonded to $R_{12}$.

14. The [optical material organic] compound according to claim 12, wherein X represents a substituent selected from the following substituents:

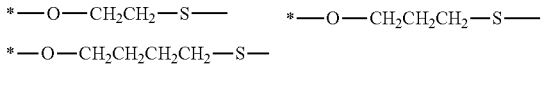

where a symbol * represents an end bonded to $R_{11}$, and

Y represents a substituent selected from the following substituents,

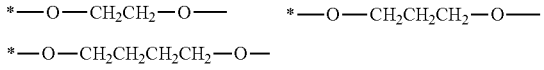

where a symbol * represents an end bonded to $R_{12}$.

15. The [optical material organic] compound according to claim 12, wherein X represents a substituent selected from the following substituents:

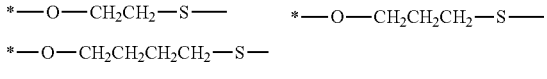

where a symbol * represents an end bonded to $R_{11}$,

Y represents a substituent selected from the following substituents,

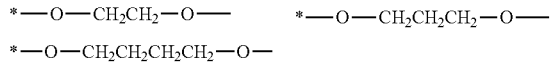

where a symbol * represents an end bonded to $R_{12}$, $R_{11}$ and $R_{12}$ represent individually a hydrogen atom or a (meth)acryloyl group, and $Z_3$ represents a substituent selected from the group consisting of a hydrogen atom, a halogen atom, an alkoxy group having the carbon number of 1 or 2, an alkylthio group having the carbon number of 1 or 2, and an alkyl group having the carbon number of 1 or 2.

16. The [optical material organic] compound according to claim 12, wherein $Z_3$ [represents an alkyl group which has the carbon number of 1 or 2 and which may have a substituent and the substituent is represented] *is represented* by the following general formula ([4] *2*):

(2)

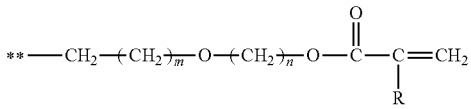

in the formula ([4] *2*), a symbol ** represents a bond, m represents 0 or 1, n represents an integer of 2 to 4, and R represents hydrogen or a methyl group.

17. The [optical material organic] compound according to claim 16, wherein m is 0.

18. [An optical] *A* material comprising the [optical material organic] compound according to claim 12.

19. An optical element produced by molding the [optical]material according to claim 18.

20. An optical material comprising a polymer and a compound contained in the polymer, wherein the compound is represented by the following general formula (1):

(1)

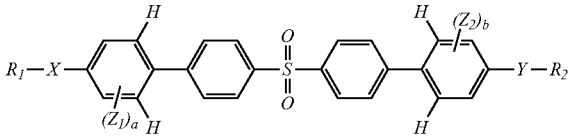

in the formula (1),

X and Y represent individually a substituent selected from the following substituents,

| | |
|---|---|
| *—S— | *—O— |
| | *—O—$CH_2CH_2$—S— |
| *—S—$CH_2CH_2$—O— | *—S—$CH_2CH_2$—S— |
| *—O—$CH_2CH_2CH_2$—O— | *—O—$CH_2CH_2CH_2$—S— |
| *—S—$CH_2CH_2CH_2$—O— | *—S—$CH_2CH_2CH_2$—S— |
| *—S—$CH_2CH_2CH_2CH_2$—S— | *—O—$CH_2CH_2CH_2CH_2$—O— |
| *—O—$CH_2CH_2CH_2CH_2$—S— | *—S—$CH_2CH_2CH_2CH_2$—O— |

where a symbol * represents an end bonded to $R_1$ or $R_2$, $R_1$ and $R_2$ represent individually a substituent selected from the group consisting of a hydrogen atom, an alkyl group having the carbon number of 1 or 2, and a (meth)acryloyl group, $Z_1$ and $Z_2$ represent individually a substituent selected from the group consisting of a hydrogen atom, a halogen atom, an alkoxy group having the carbon number of 1 or 2, an alkylthio group having the carbon number of 1 or 2, a methyl group, an ethyl group, and a methyl or ethyl group having a substituent selected from the group consisting of a (meth)acryloyloxy group, a (meth)acryloyloxyethoxy group, a 2-hydroxyethoxy group, a 2-mercaptoethoxy group, a 2-mercaptoethylthio group, a (meth)acryloyloxypropoxy group, a 3-hydroxypropoxy group, a 3-mercaptopropoxy group, a 3-mercaptopropylthio group, a (meth)acryloyloxybutoxy group, a 4-hydroxybutoxy group, a 4-mercaptobutoxy group, a 4-mercaptobutylthio group, an allyloxy group, an allylthio group, a 4-vinylbenzyloxy group, an oxiranyl methoxy group, an oxiranyl ethoxy group, a thiiranyl methoxy group, a thiiranyl ethoxy group, a methylthio group, an ethylthio group, a methoxy group, and an ethoxy group, or a substituent represented by the following general formula (2):

(2)

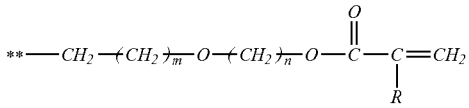

where a symbol ** represents a bond, m represents 0 or 1, n represents an integer of 2 to 4 and R represents hydrogen or a methyl group, a and b represent individually an integer of 0 to 2, two $Z_1$s may be the same or different when a is 2, and two $Z_2$s may be the same or different when b is 2.

* * * * *